United States Patent
Duhaylongsod et al.

(10) Patent No.: US 6,387,047 B1
(45) Date of Patent: May 14, 2002

(54) LOW PROFILE SUPPORT MEMBER FOR A SURGICAL RETRACTION APPARATUS

(75) Inventors: Francis G. Duhaylongsod, Honolulu, HI (US); Janice Lee Rullo, Mayfield Heights; William John Koteles, Broadview Heights, both of OH (US)

(73) Assignee: Rultract, Inc., Cleveland, OH (US)

( * ) Notice: Subject to any disclaimer, the term of this patent is extended or adjusted under 35 U.S.C. 154(b) by 0 days.

(21) Appl. No.: 09/560,835

(22) Filed: Apr. 28, 2000

Related U.S. Application Data

(60) Continuation-in-part of application No. 09/373,959, filed on Aug. 13, 1999, now Pat. No. 6,228,026, which is a division of application No. 09/224,185, filed on Dec. 31, 1998, now Pat. No. 5,984,866.
(60) Provisional application No. 60/072,240, filed on Jan. 23, 1998.

(51) Int. Cl.⁷ .............................................. A61B 17/02
(52) U.S. Cl. ........................................ 600/231; 600/228
(58) Field of Search ................................ 600/227, 229, 600/228, 230, 231

(56) References Cited

U.S. PATENT DOCUMENTS

| | | |
|---|---|---|
| 373,362 A | 11/1887 | Hamilton |
| 1,048,750 A | 12/1912 | Smith |
| 1,242,688 A | 10/1917 | Hawley |
| 1,747,799 A | 2/1930 | Straus .................... 600/228 |
| 1,914,202 A | 6/1933 | Henze et al. |

(List continued on next page.)

FOREIGN PATENT DOCUMENTS

| | | | |
|---|---|---|---|
| SU | 232451 | 12/1968 | |
| SU | 1210800 | 2/1986 | .................. 600/228 |

OTHER PUBLICATIONS

Rultract Incorporated, Circulator Applied Internal Mammary Artery Retractor advertisement (undated).
Stille Stainless Steel Retractors catalog dated Dec. 18, 1939.
KNY Scheerer Corp., Catalog of Surgical Instruments dated 1959, pp. 70–75 and 90–92.

(List continued on next page.)

Primary Examiner—Paul J. Hirsch
(74) Attorney, Agent, or Firm—Renner, Otto, Boisselle & Sklar, LLP

(57) ABSTRACT

In one embodiment, the present invention relates to a low profile support member for a surgical retraction apparatus which includes a support member in which a lower portion of the support member has a rectilinear portion for insertion into an anchoring receptacle; an upper portion of the support member has a first horizontal extension; a splined coupling adaptor connects together the lower and upper portions, in which the splined coupling adaptor includes a splined segment having a key-like splined portion and a lock-like splined portion; and an extender portion having both a vertical extension and a second horizontal extension. The extender portion is mountable on the first horizontal extension. In one embodiment, the present invention relates to a method of providing surgical retraction to a patient positioned relative to a support platform, including steps of mounting upper and lower portions of a support member with respect to each other by a lock-and-key-like splined connection and with respect to the platform, in which the upper portion includes a first horizontal extension; mounting on the first horizontal extension an extender portion which has both a vertical extension and a second horizontal extension; positioning a lifting device above the patient by mounting the lifting device with respect to the second horizontal extension; and applying retraction to the patient.

16 Claims, 10 Drawing Sheets

U.S. PATENT DOCUMENTS

| | | | |
|---|---|---|---|
| 3,403,675 A | | 10/1968 | Carr |
| 3,643,655 A | | 2/1972 | Peronti |
| 3,710,783 A | | 1/1973 | Jascalevich |
| 3,823,709 A | | 7/1974 | McGuire |
| 4,099,521 A | | 7/1978 | Nestor et al. |
| 4,143,652 A | | 3/1979 | Meier et al. |
| 4,151,838 A | | 5/1979 | Crew |
| 4,457,300 A | | 7/1984 | Budde .................. 600/228 |
| 4,622,955 A | | 11/1986 | Fakhrai |
| 4,702,465 A | | 10/1987 | McConnell |
| 4,865,019 A | | 9/1989 | Phillips |
| 4,953,540 A | | 9/1990 | Ray et al. |
| 4,971,038 A | | 11/1990 | Farley |
| 5,088,472 A | | 2/1992 | Fakhrai |
| 5,109,831 A | | 5/1992 | Forrest et al. |
| 5,545,123 A | | 8/1996 | Ortiz et al. |
| 5,613,939 A | | 3/1997 | Failla |
| 5,876,333 A | | 3/1999 | Bigliani et al. |
| 5,984,866 A | * | 11/1999 | Rullo et al. ............ 600/231 |
| 6,228,026 B1 | * | 5/2001 | Rullo et al. ............ 600/231 |

OTHER PUBLICATIONS

Transaxillary Approach for First Rib Resection to Relieve Thoracic Outlet Syndrome, David B. Roos, M.D., from the Department of Surgery, University of Colorado School of Medicine, Annals of Surgery, Mar. 1966.

Thoracic Outlet Syndrome, David B. Roos, M.D. and J. Cuthbert Owens, M.D., Arch Surg—vol. 93, Jul. 1966.

The Surgical Armamentarium, V. Mueller, dated 1973, pp.68, 281, 346, 347.

The Surgical Armamentarium, American V. Mueller, dated 1980, pp.74, 75, 78, 87, 88.

Codman & Shurtleff, Inc., Catalog for Surgical Products dated 1984 pp. 431–437.

Copending U.S. application Ser. No. 09/235,704, filed on Jan. 22, 1999.

Thoracic Outlet Syndrome, David B. Roos, M.D. and J. Cuthbert Owens, M.D., Arch. Surg. vol. 93, Jul., 1966.

* cited by examiner

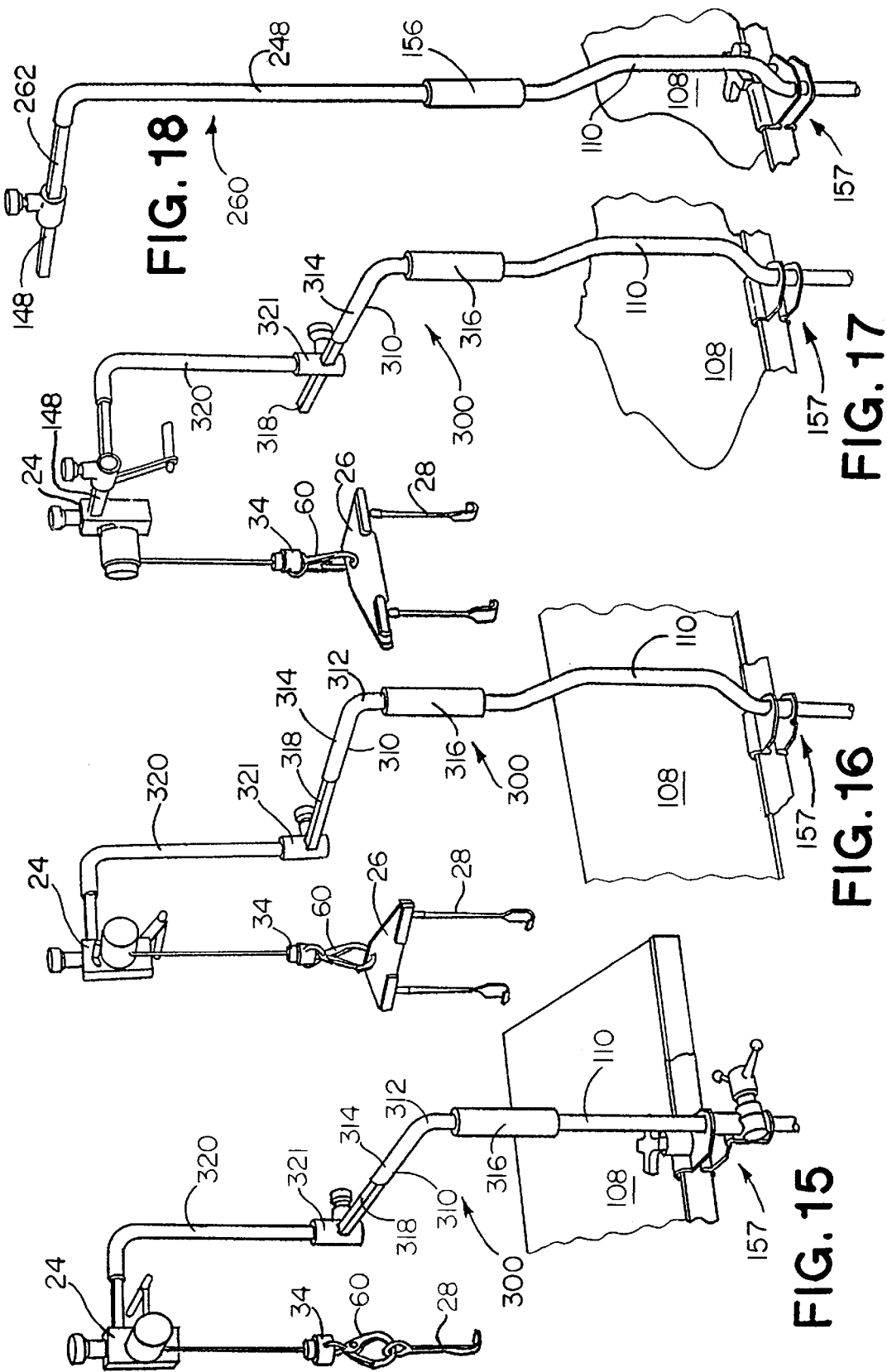

LOW PROFILE SUPPORT MEMBER FOR A SURGICAL RETRACTION APPARATUS

CROSS-REFERENCE TO RELATED APPLICATIONS

The present application is a continuation-in-part of application Ser. No. 09/373,959, now U.S. Pat. No. 6,228,026, which is a divisional of Ser. No. 09/224,185, now U.S. Pat. No. 5,984,866, and claims benefit of Prov. No. 60/072,240 filed Jan. 23, 1998.

Reference is hereby made to the following applications copending herewith, the disclosure of each of which is hereby incorporated by reference in its entirety: SURGICAL SUPPORT APPARATUS WITH SPECIALIZED RAKES, Ser. No. 09/235,704, now U.S. Pat. No. 6083,153; SURGICAL SUPPORT APPARATUS WITH ADJUSTABLE RAKE AND ADJUSTABLE CABLE LIFTING DISK, Ser. No. 09/235,172, now U.S. Pat. No. 6,090,042; and SURGICAL SUPPORT APPARATUS WITH A Z-SHAPED RAKE PLATE, Ser. No. 09/235,840, now U.S. Pat. No. 5,964,699.

FIELD OF THE INVENTION

The present invention relates generally to surgical instruments for holding and elevating body parts and/or for maintaining a clear opening to a body area during surgery, particularly thoracic surgery. More specifically, the present invention relates to support apparatus upon which surgical devices, such as retractors and the like, may be operably mounted.

BACKGROUND OF THE INVENTION

In the performance of surgery in the chest cavity, generally referred to as thoracic surgery, it is desirable to hold open the surgical cavity to allow access to the organ or body part upon which the surgery is being performed. This is especially important in the case of cardiac surgeries. An early example of a surgical retractor for use in coronary bypass surgical procedures which include dissection of the internal mammary artery is disclosed in U.S. Pat. No. 4,622,955, which is incorporated by reference.

In the device of U.S. Pat. No. 4,622,955 plural rakes which engage the body and retract the surgical cavity formed by a midsternotomy are relatively fixedly positioned with respect to each other from a rod. The rod may be elevated or lowered, as desired. However, there is no adjustment for the rakes relative to the rod, to each other or to the surgical cavity. Furthermore, the rakes are generally small, having sharply pointed tips and are generally designed to be employed in pairs for the purpose of retracting one side of a sternum which has been split by a midsternotomy. The device of U.S. Pat. No. 4,622,955 cannot provide the support required for other procedures which have been recently developed as alternatives to the midsternotomy approach to the coronary bypass, and it is not adapted for use in reoperative midsternotomy procedures.

It is well known and appreciated that in surgical procedures, time is of the essence, and delays associated with adjustments of support equipment are unwanted. Additionally, during certain procedures, it may be desirable to impose or to change a biasing force on a body portion which is undergoing a surgical procedure or treatment. Further, it is desirable to minimize the number of personnel required to assist in performance of a surgical procedure, to minimize the number of personnel who must enter the sterile field, and to minimize the tasks, such as holding a retractor, of personnel during surgical procedures. Further, it is desirable to have available to the surgeon instruments appropriately adapted to each type of procedure.

Coronary Bypass Surgery: The Midsternotomy

Coronary bypass surgery, in which the internal mammary artery is harvested from the chest wall and used for anastomosis of a vessel to bypass poorly functioning coronary arteries, has been performed thousands of times and has become an almost routine procedure for cardiac surgeons. Since the inception and throughout the development of the procedure, coronary bypass surgery has required a midsternotomy to allow access to the heart and coronary arteries. In the midsternotomy, an initial incision is made from the manubrium of the sternum to a point toward the xiphoid. Next, the sternum is split down the middle by means of a reciprocating sternal saw in order to allow access to the coronary arteries and the internal mammary artery. It has been estimated that in 1988, some 350,000 midsternotomy procedures were performed for coronary bypass surgery.

In performing the coronary bypass procedure, following the midsternotomy, it is necessary to retract one side of the split sternum in order to gain access to the thoracic cavity, and particularly to the internal mammary artery. Either the left or right internal mammary artery may be harvested for the bypass, so either side of the chest may need to be retracted. Retractors have been developed in order to provide the requisite retraction of the split sternum. An early example is disclosed in U.S. Pat. No. 4,622,955. The RULTRACT® internal mammary artery retractor is a more advanced retractor which has been developed to allow left or right internal mammary artery exposure in the undersurface of the chest wall. The RULTRACT® internal mammary retractor has been extensively used in coronary bypass surgery. The RULTRACT® retractor is not limited to coronary bypass surgery, having been used in various other thoracic surgical procedures, such as lung reduction and pericardial drainage.

The RULTRACT® internal mammary retractors include a rake plate and two or possibly three rakes. Most frequently, in use the two rakes are applied to one side of the opening formed by a midsternotomy and the rake plate is attached to a lifting device. The lifting device lifts the rake plate and the rakes, applying an upward and outward retraction to the sternum by which the surgical cavity is opened. The sternum is securely held in the open position when the lifting device is locked in position. This exposes the entire course of the mammary artery from its origin to its bifurcation, allowing its dissection. The rakes in the conventional retractor have a relatively small radius of curvature and have quite sharp tips to provide a secure attachment to the sternum. With the sternum securely held in the open position, the coronary artery dissection may then be carried out by the surgeon. In the standard midsternotomy, the retractor provides good exposure and allows the surgeon sufficient access for the dissection of the mammary artery.

After the coronary artery has been harvested, the RULTRACT® retractor is removed and a sternal retractor is placed in the chest and the grafting and anastomoses is performed. Closure is normally accomplished in this procedure by applying wires or staples to the sternum to hold it together in the properly aligned position for healing.

The midsternotomy is a highly invasive procedure, and much of the difficulty in recovering from a coronary surgical procedure involving a midsternotomy is due to the trauma resulting from the midsternotomy rather than to any trauma inflicted upon the coronary arteries or other thoracic organs and structures. As a result, a need has been identified for a less invasive procedure which will provide the surgeon with access to the coronary and internal mammary arteries with a minimum of trauma to the thoracic region.

The Mid-Cab, a Less Invasive Procedure

A less invasive procedure which has been developed to provide access to the mammary artery and the coronary arteries for coronary bypass surgery is known as the mid-cab or minimally invasive technique. In the mid-cab, an incision is made between the third and fourth rib, in the third intercostal space. The fourth rib is released from the sternum, and the incision is retracted downward by attaching a retractor rake to the fourth rib. A second retractor rake is next attached to the third rib, which is retracted upward and in the cranial direction. With access thus provided to the third rib and in the direction of the upper chest, the surgeon is able to create an opening from the third rib to the first rib or subclavian region. Via this opening, the surgeon is provided with access to the mammary artery, which is progressively dissected from the chest wall as the opening is progressively advanced toward the first rib. With the development of this procedure, a need has been identified for more advanced retractors specially adapted to the mid-cab procedure, and particularly for a retractor which can simultaneously retract the third and fourth ribs in different directions.

It is well known among cardiac surgeons that the position of the internal mammary artery in the chest is variable from patient to patient. For this reason, during the mid-cab procedure, it is sometimes necessary for the surgeon to manipulate the chest wall to provide adequate access to the mammary artery. The surgeon may have to either elevate or depress the chest wall in the region of the first rib in order to gain access to the mammary artery so that it can be dissected in this procedure. Thus, a need has been identified for devices which can assist the surgeon in the less invasive mid-cab procedure, particularly including a retractor capable of two-direction retraction at the site of the intercostal incision and devices for providing elevation and/or depression of the clavicle and first rib region of the chest wall.

Reoperative Coronary Bypass Surgery

As coronary surgery has become increasingly prevalent and postoperative coronary rehabilitation more successful, a larger number of patients are surviving longer than the expected patency of their graft conduits. This has resulted in an increasing number of patients having to undergo a second coronary bypass procedure. The second, or reoperative, procedure has sometimes been referred to as a "re-do" procedure. Unfortunately, the re-do midsternotomy is neither as simple nor as safe as the initial procedure. This is primarily due to the scarring and resultant adhesions which develop between the internal side of the sternum and the underlying organs and tissues of the thoracic cavity following the initial midsternotomy. When the re-do midsternotomy is performed by essentially repeating the steps of the initial procedure, an increase in morbidity and mortality has been observed. Thus, a need has arisen for an alternative procedure.

An alternative procedure which has been adapted to coronary surgery in order to avoid the dangers of the re-do midsternotomy is known as a xiphoid entry. In the xiphoid entry, an initial incision is made along the scar from the previous midsternotomy to a point midway between the xiphoid and the umbilicus. The old sternal wires are removed. The xiphoid process is excised. A single retractor rake is applied to the caudal end of the sternum and the sternum is firmly retracted in an anterior and cranial direction. This allows the surgeon to directly visualize the anterior retrosternal space, so that the retrosternal adhesions can be taken down. The surgeon progressively takes down the adhesions toward the subclavian, until the sternum is freed from the underlying organs. Once this is done, the retractor may be removed and the sternum divided with a reciprocating sternal saw as in the original procedure.

During the retraction particular care must be exercised since, first, the quite sharp rake tips of the standard retractor are applied directly to the lower end of the sternum from which the xiphoid process was excised, and second, a very strong lifting force is required to elevate the entire sternum. The possibility of unintended trauma to the sternum exists. A second problem which has been experienced with the procedure described above is that the entire retractor plate and the extra, non-used rake must be suspended in a central location in the operating field, further obstructing the work area with its already limited space available. A third problem is that due to the rake plate and various parts attaching it to the lifting apparatus, the retraction force applied to the sternum is not transmitted in a simple straight line from the lifting apparatus to the sternum. Thus, a need has been identified for a rake which is more appropriately adapted to the xiphoid entry in a re-do coronary bypass procedure.

In the procedures described in the foregoing and in additional thoracic surgical procedures, the surgeon may be required to adapt the support apparatus for retraction of the patient's body in several directions at once. In such an instance, a single retractor held by a single support device may not be sufficient to provide the retraction required by the surgeon. Furthermore, it may be helpful to the surgeon to combine various embodiments of retraction devices in order to adequately obtain the retraction required.

As an example of a surgical application requiring a retraction device particularly adapted to the individual use, in pediatric surgery it is often necessary to introduce novel techniques due to small size of the patient. Procedures and devices designed for adult patients are frequently not useable with pediatric patients. For example, it may be necessary to adjust the angle of and direction from which retraction is applied, which in turn requires significant change in the retraction support apparatus.

Accordingly, there is a strong need in the art for surgical retractor apparatus with which to facilitate the development and implementation of new surgical procedures, particularly less invasive procedures such as the mid-cab coronary artery bypass procedure, for more radical thoracic procedures, such as a lung reduction or other procedures, and for specialized procedures, such as thoracic and other surgeries, performed upon, e.g., pediatric patients.

SUMMARY OF THE INVENTION

The present invention, in one embodiment, relates to a low profile support pole for a retractor support system which includes a splined coupling, by which both the exact angle at which the retraction device is suspended with respect to the "head-to-toe" direction of the patient's body, and the exact elevational angle at which the retraction device is applied with respect to the horizontal plane of the patient's body, may be selected and reliably retained without the possibility of slippage, and while providing the maximum access to the patient and the minimum interference with the surgical team's movements during the surgical procedure.

The splined coupling allows for adjustment of the "head-to-toe" angle, and the low-profile support pole allows for adjustment of the horizontal angle, and both may be adjusted during the course of a surgical procedure. As a result, the surgeon may better adapt to the changing conditions and needs of the patient. The present invention is particularly useful for a partial sternotomy.

In the embodiment of the present invention mentioned in the previous paragraph, the apparatus includes a generally vertically extending support member for a surgical retraction apparatus which includes a lower portion of the support member having a rectilinear portion for insertion into an anchoring receptacle, an upper portion of the support member having a low-profile first horizontally extending portion, an extender bar with a further vertically extending portion and a second horizontally extending portion, and a splined coupling adaptor for connecting the lower portion of the support member to the upper portion having a low-profile first horizontally extending portion. The splined coupling adaptor comprises a splined segment having lock- and key-like splined portions. The splines may be involute. Preferably the key-like splined segment is disposed on the lower portion of the support member. Alternatively, the key-like splined segment may be disposed on the upper portion of the support member. In one embodiment, each splined segment comprises at least 12 teeth. In one embodiment, each splined segment comprises at least 19 teeth.

The present invention includes surgical retraction devices which may be selected and quickly implemented as required in an individual surgical procedure depending on the particular patient's needs. These devices allow the surgeon to perform a less-invasive procedure while retaining the option to easily switch to the more radical surgical procedures, or to make other adaptations as necessary, in the event of unforeseen difficulties. When the RULTRACT® retractor system and the devices of the present invention are employed, the surgeon is provided with a greatly improved degree of adaptability in the procedures chosen during a particular surgical procedure, with a minimum change of retraction apparatus.

Thus, the present invention, in one embodiment, relates to a low profile support member for a surgical retraction apparatus, including a lower portion mountable on a support platform; an upper portion of the low profile support member having a first horizontal extension; a splined coupling adaptor for connecting the lower portion and the upper portions, wherein the adaptor comprises a splined segment having a key-like splined portion and a lock-like splined portion; and an extender portion having both a vertical extension and a second horizontal extension, the extender portion mountable on the first horizontal extension. In another embodiment, the extender portion further includes a clamp and a receptacle for receiving the first horizontal extension. In another embodiment, the receptacle is disposed such that the second horizontal extension is mounted at a right angle to the first horizontal extension. In another embodiment, the first horizontal extension is directly connected to the splined coupling adaptor with relatively minimal vertical rise therebetween. In another embodiment, the first horizontal extension is directly connected to the splined coupling adaptor substantially free of vertical rise therebetween. In another embodiment, a base portion of the low profile support member is just long enough to fit securely in and be attached to the splined coupling adapter. In another embodiment, the splined coupling adaptor enables the first horizontal extension to be securely aligned at one of a plurality of selected angles with respect to the anchoring receptacle.

The present invention, in one embodiment, relates to a method of providing surgical retraction to a patient positioned relative to a support platform, including the steps of mounting upper and lower portions of a low-profile support member with respect to each other by a lock-and-key-like splined connection and with respect to the platform, the upper portion comprising a first horizontal extension; mounting on the first horizontal extension an extender portion having both a vertical extension and a second horizontal extension; positioning a lifting device above the patient by mounting the lifting device with respect to the second horizontal extension; and applying retraction to the patient. In another embodiment, the step of mounting further comprises selecting a desired angle of orientation between the first horizontal extension and the support platform. In another embodiment, the step of mounting further comprises selecting a desired angle from which retraction is applied to the patient. In another embodiment, the step of mounting on the first horizontal extension an extender portion places the vertical extension in a position substantially aligned with a patient midline plane.

The present invention, in one embodiment, relates to a method of providing surgical retraction to a patient positioned relative to a support platform, including the steps of positioning a lifting device above the patient, said positioning comprising mounting the lifting device on a multiple part generally vertically extending low profile support member which has a lock-and-key-like splined connection between at least two of the multiple parts, the support member comprising a first horizontal extension, and mounting on the first horizontal extension an extender portion having both a vertical extension and a second horizontal extension; adjusting the position of the lifting device relative to the patient by selecting an angular relation between a first one of the parts and a second one of the parts at the lock-and-key-like splined connection; and applying retraction to the patient. In another embodiment, the step of mounting includes placing the lifting device on the second horizontal extension. In another embodiment, the step of mounting further includes selecting a desired angle of orientation between the first horizontal extension and the support platform. In another embodiment, the step of mounting further comprises selecting a desired angle at which retraction is applied to the patient. In another embodiment, the step of mounting on the first horizontal extension an extender portion places the vertical extension in a position substantially aligned with a patient midline plane.

The present invention, in one embodiment, relates to a low profile support member for a surgical retraction apparatus, including a lower portion mountable on a support platform; an upper portion of the low profile support member having a first horizontal extension; a splined coupling adaptor for connecting the lower portion and the upper portions, wherein the adaptor comprises a splined segment having a key-like splined portion and a lock-like splined portion; and an extender bar, the extender bar mountable on the first horizontal extension. In another embodiment, the low profile support member further includes a lifting device mounted on the extender bar. In another embodiment, the lifting device includes a cable which, in use, forms an acute angle between the cable and the support platform.

Using a retractor with a low profile support member in accordance with the present invention, if desired, the retraction effort can be applied at a more acute angle than with the higher profile retractor. Also, there is greater available area in the surgical field for the surgical team to move about and to operate on the patient during the surgical procedure, this being especially advantageous in the case of surgeries for relatively small size patients, such as children.

The low profile support member of the present invention, as described below, allows use of a surgical retraction device and is particularly adaptable to specialized uses such as pediatric surgery, in which it may be necessary to introduce novel techniques due to relatively small size of the patient. The low profile support member, used as described below, allows a surgeon to adapt surgical procedures and apparatus originally designed for adult patients for use with pediatric patients. For example, the low profile support member of the present invention allows the surgeon to adjust the angle of and direction from which retraction is applied. Thus, by changing the support member from a standard, relatively high support, the surgeon can adapt surgical procedures and apparatus to additional uses, such as pediatric surgery, without being forced to make significant changes in the retraction apparatus.

As additional significant benefit of the low profile support member and the methods of using it described below is the additional space in the surgical field which is made available. Because a significant portion of the vertical aspect of the low profile support member is located toward the center, away from the sides, of the surgical support platform, the surgical team is allowed more "elbow room" in the area in which they must stand, the sides of the surgical support platform.

To the accomplishment of the foregoing and related ends, the invention then comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF THE DRAWINGS

FIGS. 15–17 are perspective views of several embodiments of the low profile support member and the extender portion with a retractor apparatus mounted on the horizontal extension of the extender portion;

FIG. 18 is a perspective view of an embodiment of a standard profile support member;

DETAILED DESCRIPTION

Figure 1:
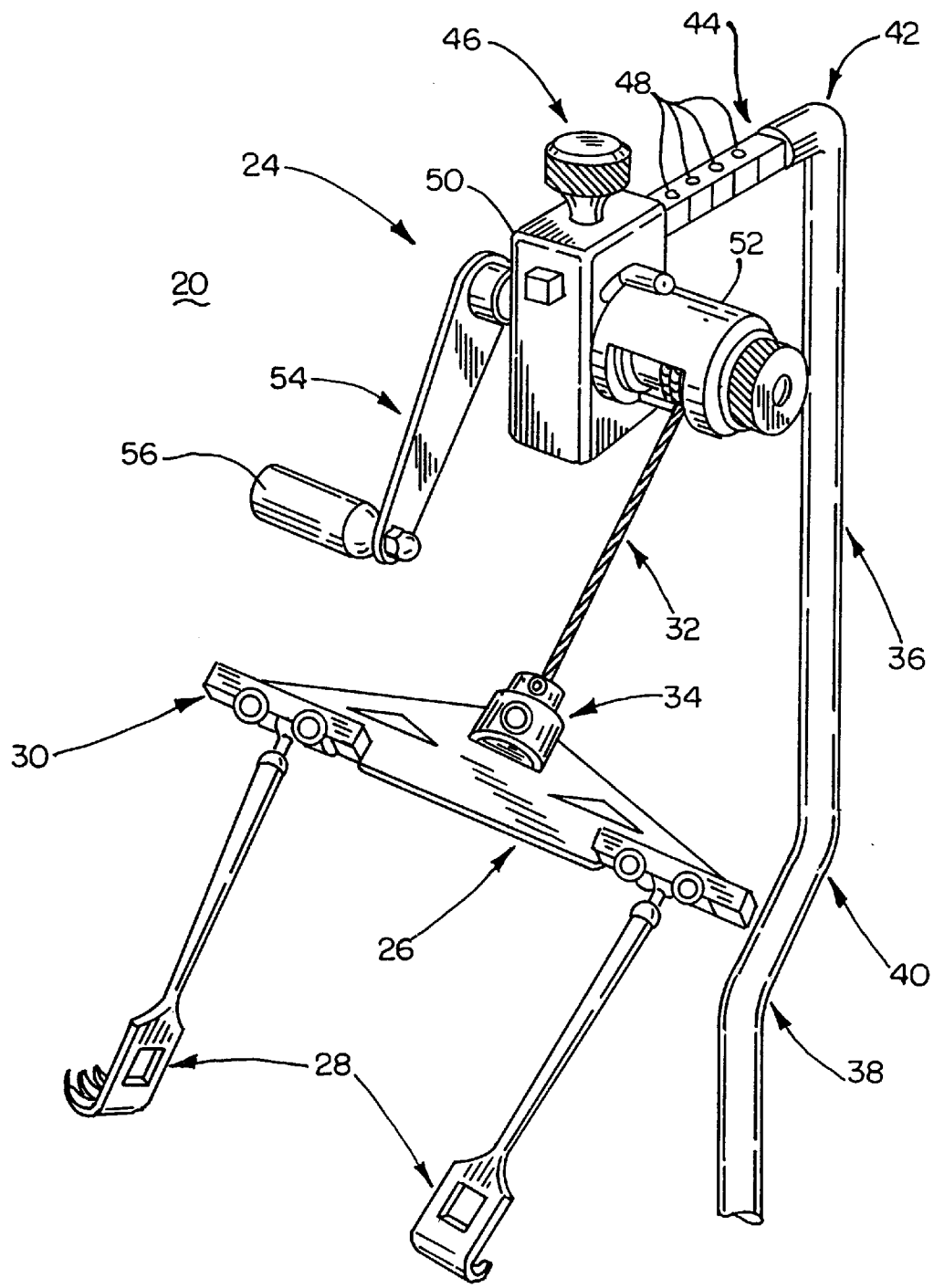
FIG. 1 is a perspective view of a conventional Rultract® surgical retractor.

The present invention will now be described with reference to the drawings wherein like reference numerals are used to refer to like elements throughout. As mentioned above, the present invention relates to surgical instruments for holding open a body part during surgery, for example, to maintain open and clear a surgical cavity during surgery, particularly including cardiac surgery or other thoracic surgery. In all embodiments described hereinafter, the preferred material of construction is stainless steel, preferably 304 stainless steel, which has good strength and sterilization characteristics and is resistant to corrosion even after many cycles of use, cleansing and sterilization.

Referring to FIG. 1, a conventional RULTRACT® retractor and surgical support assembly 20 are shown. The RULTRACT® retractor includes a lifting device 24, a rake plate 26, at least one rake 28 for applying retraction to a patient's body, and pivoting mounting means 30 for mounting the rakes 28 to the rake plate 26. The rake plate 26 is attached to the ratcheting lifting device 24 by a cable 32. The cable 32 is attached to the rake plate 26 by a pivot hub connector 34.

The rake plate 26 and the rakes 28 associated therewith may be raised or lowered via the cable 32, which is connected to the lifting apparatus 24. As described below the RULTRACT® system may include a ratcheting lifting device 24, available from RULTRACT, INC., Cleveland, Ohio, although other lifting devices could be used. As shown in FIG. 1, a pivot hub connector 34 allows the rake plate 26 to rotate relative to the cable 32 to facilitate positioning of the rakes 28 relative to the surgical cavity of the patient without twisting the cable 32, which could result in a torque applied to the retractor rake plate 26, which undesirably could be transmitted to the patient's body.

In the conventional RULTRACT® retractor assembly 20, the ratcheting lifting device 24 is mounted on a support pole 36. Although not shown in FIG. 1, the support pole 36 is mounted at its lower end to a surgical table by conventional means. As shown in FIG. 1, the support pole 36 includes bends 38 and 40 which dispose outward the portion of the support pole 36 which is above the level of the surgical table so as to allow additional space in the surgical field around the patient. At the upper end of the pole 36, is a right-angled bend 42 connecting the support pole 36 to a horizontally extending portion 44. The horizontally extending portion 44 extends outwardly above the patient, so that the retraction force is applied at least partially in an upward direction. Since the lifting device 24 is not aligned with the patient's midline, the retraction is applied partially outwardly laterally with respect to the patient.

In this embodiment, the lifting device 24 is mounted on the horizontal extension 44. The lifting device 24 includes a securing bolt 46 by which the lifting device 24 is securely positioned on the extension 44. To facilitate quick and sure positioning of the lifting device 24 on the extension 44, a plurality of bores 48 are provided, into which an end of the securing bolt 46 may be inserted. The bores 48 allow for precise horizontal adjustment of the position of the lifting device 24 relative to the patient and the surgical field.

The ratcheting lifting device 24, as shown in FIG. 1, includes a ratcheting winch assembly 50 for reeling in the cable 32. The cable 32 is attached to and may be reversibly wrapped around a spool (not shown) extending outwardly from the winching assembly 50. The spool around which the cable 6 wraps is partially enclosed by a housing 52. The opposite end of the spool is attached to, and the winching assembly is actuated by, the crank arm 54 and crank handle 56, in conventional fashion.

In the following description of the present invention, like reference numbers refer to like parts. The lifting device and support arm used in the present invention are essentially the same as the conventional assembly described above and will not be further described except as necessary to indicate the functioning of the present invention relative thereto.

Figure 2:
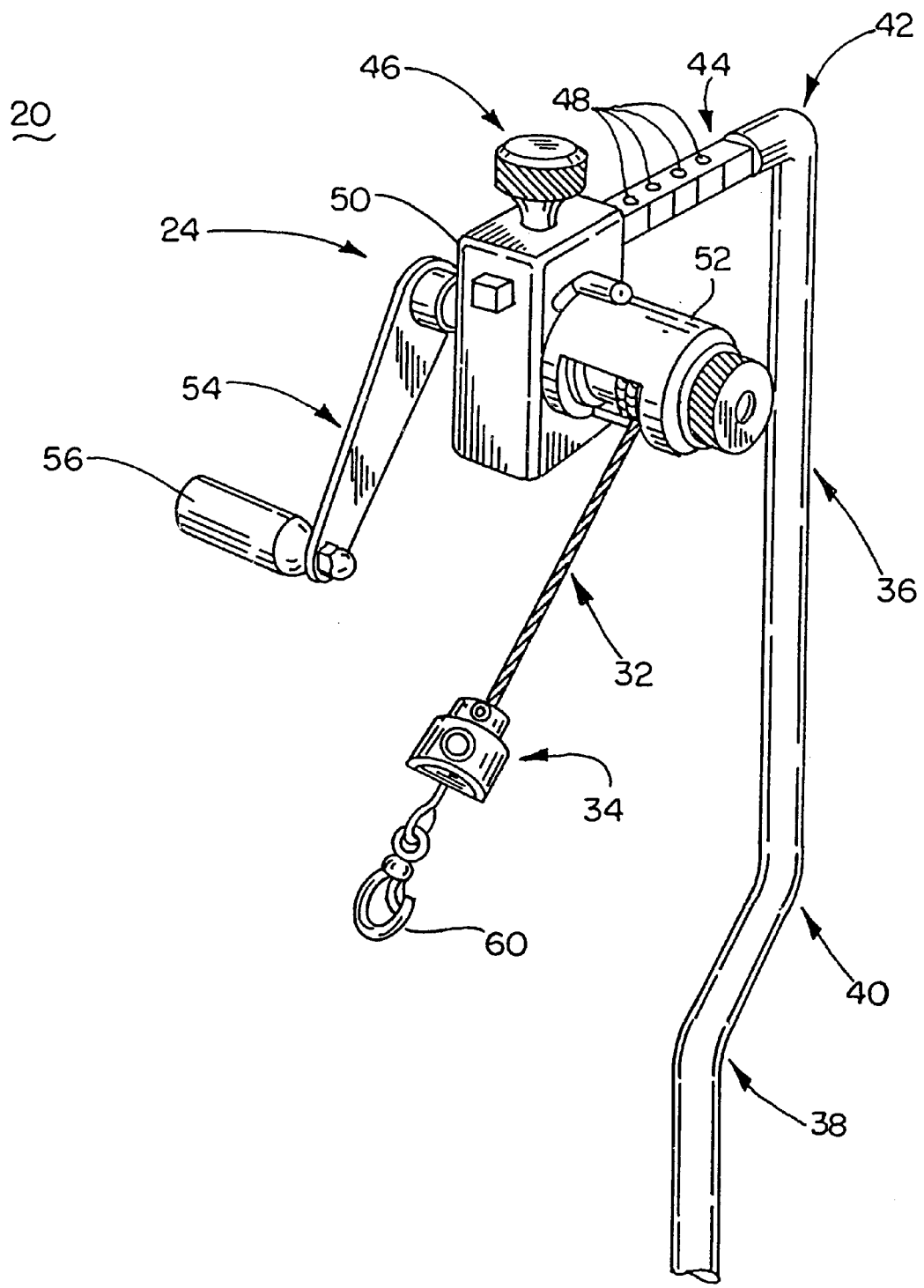
FIG. 2 is a perspective view of a conventional Rultract® retractor support and lifting apparatus with a swiveling hub and snap clip for attaching a rake plate or individual rakes.
Figure 3A:
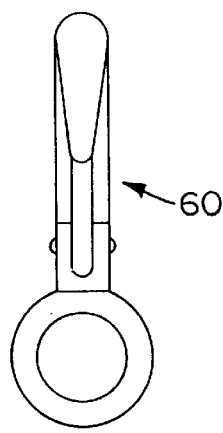
FIGS. 3A and 3B are respectively front and side elevational views of a snap clip as used in an embodiment of the present invention.
Figure 3B:
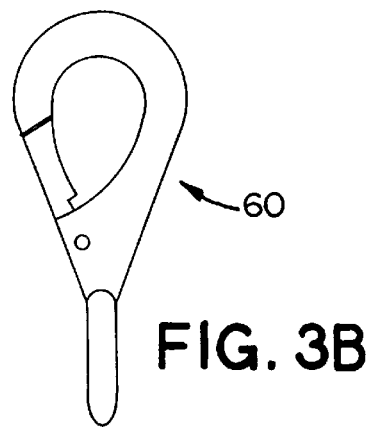

In the present invention, the ratcheting lifting device 24 may be similar to the ratcheting device 24 shown in FIG. 1 and available from RULTRACT, INC., Cleveland, Ohio. Referring to FIG. 2, in an alternative embodiment of the RULTRACT® surgical support assembly, the ratcheting lifting device 24 has the cable 32 attached thereto, as described above with reference to FIG. 1. As shown in FIG. 2, the free end of the cable 32 may have attached thereto a pivot hub connector 34 and a snap ring 60. The snap ring 60 may be used for attaching the rakes or retraction apparatus to the cross bar assembly of the present invention. The snap ring 60 provides a secure, but quickly releasable attachment between the lifting device 24 and the rakes or retraction apparatus used with the present invention. FIGS. 3A and 3B show respectively front and side elevational views of the snap clip 60 shown in FIG. 2, and which is exemplary of such a quick-release device which may be used in accordance with the present invention. Other quick-release devices known in the art may be substituted for the snap ring 60.

Similarly, the support bar 36, including the horizontal extension 44, as shown in FIGS. 1 and 2, is the starting point both for one embodiment of the first embodiment of the present invention, a cross bar assembly which employs couplings and an extension bar, and for a second embodiment of the present invention, a "head-to-toe" extension bar which extends at right angles from the horizontal extension 44. The support pole 36 may also incorporate the third embodiment of the present invention, a splined coupling for a support bar. Each of these embodiments are described in more detail below.

Figure 4:
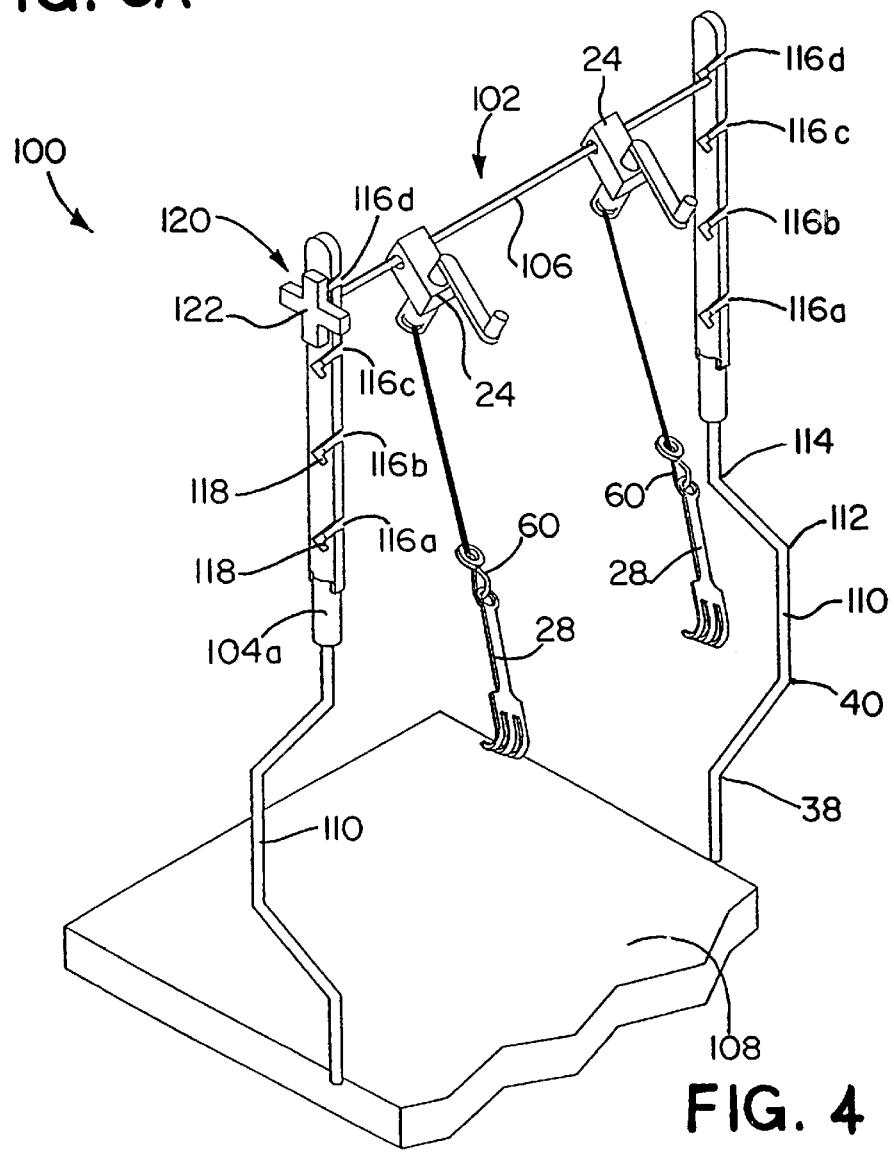
FIG. 4 is a perspective view of a cross bar support assembly in accordance with the first embodiment of the present invention.

In FIG. 4 a cross bar support system 100 is shown including a cross bar assembly 102, which includes vertical support members 104a and 104b and a cross bar 106. The cross bar assembly 102 is mounted on a patient support platform 108, which may be, for example, an operating table. The cross bar assembly 102 includes a horizontally extending cross bar 106. In FIG. 4, the cross bar 106 is shown with two ratcheting lifting devices 24 mounted on the cross bar. The preferred ratcheting lifting devices 24 are the same as those shown in FIGS. 1 and 2, which are commercially available from RULTRACT, INC., Cleveland, Ohio. Of course, other equivalent ratcheting lifting devices may be substituted for the RULTRACT® devices, if such equivalent devices are capable of being mounted on the cross bar assembly 102. Further, any number of ratcheting lifting devices 24 may be mounted on the cross bar 106, as needed for a given surgical procedure, and limited only by the space available on the cross bar 106. The ratcheting lifting device 24 may be attached for retraction either to a retractor assembly, such as a rake plate 26 with a plurality of rakes 28, such as shown in FIG. 1, or to a single retractor rake 28, as shown in FIG. 4. Referring still to FIG. 4, the cross bar 106 is attached to and is supported by the pair of vertically extending support members 104a and 104b, such that the cross bar 106 extends across a patient support platform 108. The vertical support members 104a and 104b are essentially identical, except that they are mirror images of each other. Each vertical support member 104a and 104b includes an outwardly extending portion 110 similar to the outward curve resulting from the bends 38 and 40 shown in FIGS. 1 and 2 and described above. Like the support apparatus in FIGS. 1 and 2, the outwardly extending portion 110 shown in FIG. 4 includes bends 38 and 40. However, unlike the apparatus shown in FIGS. 1 and 2, in the embodiment of the cross bar assembly 102 shown in FIG. 4, the outwardly extending member 110 includes additional bends 112 and 114, by which the vertical support members 104a and 104b are shifted inwardly back to the approximately same vertical position of the lower attached portion of the members 104a and 104b. The outwardly extending portion 110 provides additional stability to the support members 104a and 104b.

In an alternate embodiment, the vertical support members do not include the additional bends 112 and 114, so that the upper portion of the vertical support remains further outboard relative to the patient support platform 108, by a distance determined by the bends 38 and 40. In another alternate embodiment, the vertical support members do not include any outwardly extending portion, so that there are no bends such as the bends 38, 40, 112 and 114 of this embodiment.

Figure 5:
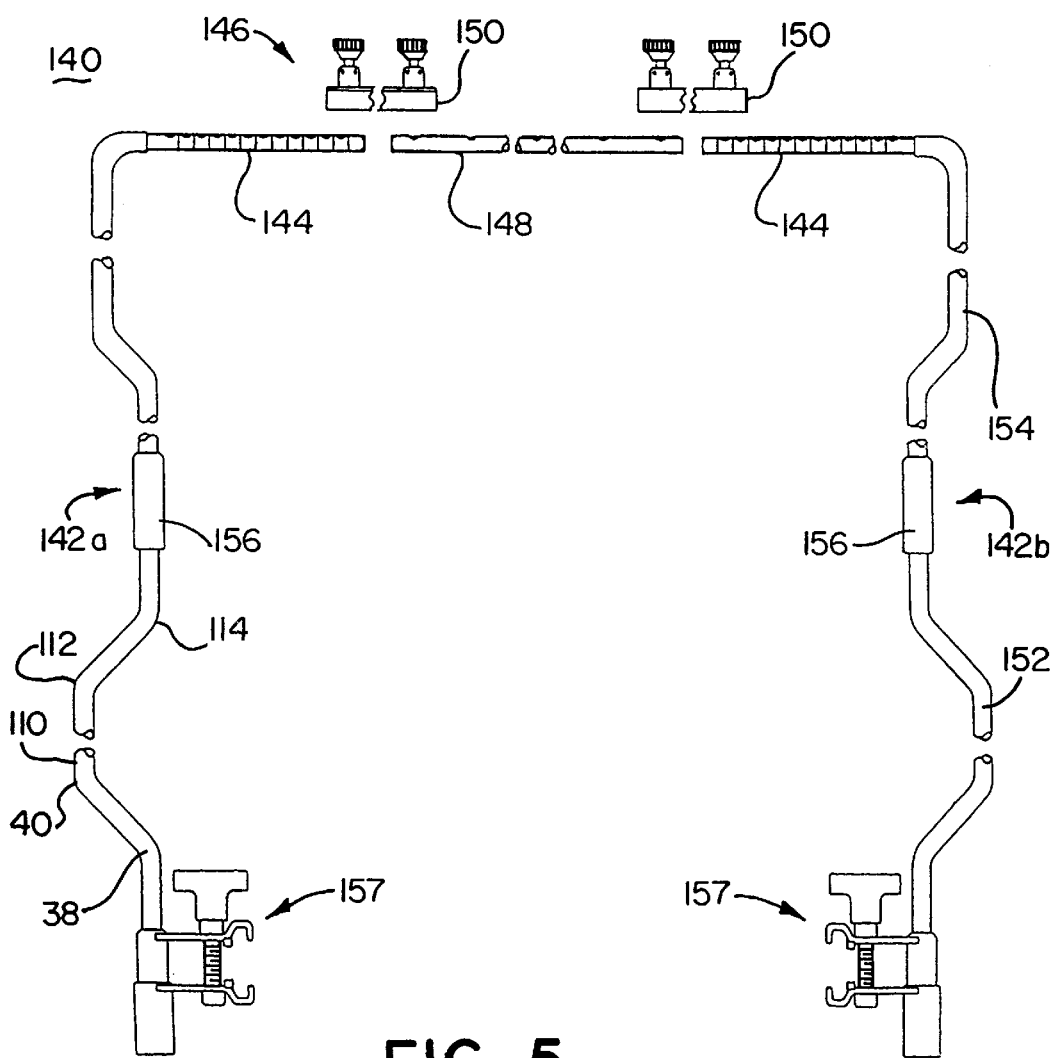
FIG. 5 is a side elevational view of another embodiment of the cross bar support assembly in accordance with the present invention partially dismantled.

The support members 104a and 104b are each releasably attachable to the patient support platform 108. The attachment means is not shown in FIG. 4, but may generally be any conventional attachment device, such as a compression clamp, as used for clamping other support bars and other surgical equipment to the operating table. An example of an attachment clamp is shown in FIG. 5 and described with respect thereto below.

As is apparent from FIG. 4, the cross bar support system 100 is quite stable, due to the cross bar 106 connecting together the support members 104a and 104b. Accordingly, it is not necessary that the support members be attached to the platform 108 by a device which restricts the rotation of the support members, such as will be described below in relation to another embodiment of the present invention. An example of a clamping device by which the vertical support members may be attached to the operating table or other patient support system is shown in FIG. 5 and described below.

Referring again to FIG. 4, the cross bar member 106 is made from metal stock which is polygonal in cross-section, having at least two opposing, parallel flat sides. For example the stock may be square, rectangular, hexagonal or octagonal. In one embodiment, the stock is about ½ inch by ½ inch square (about 12.5 mm×12.5 mm). In coordination therewith, the ratcheting lifting devices 24 include a square opening of appropriately matching size so that the devices 24 can be mounted on the cross bar 106. Thus, for example, the opening in the device 24 may be approximately 12.6 mm square, to accommodate some slight variation in the size of the cross bar 106, but to avoid any excess of free movement. It is noted that while the stock is square in this embodiment, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

As shown in FIG. 4, the vertical support members 104 each include a plurality of slots 116a, 116b, 116c and 116d. Although four such slots 116 are shown on each support member 104, any suitable number may be selected, and the invention is not limited to a particular number of such slots.

As shown in FIG. 4, each slot 116 is cut into the vertical support member 110 at a downward angle, so that the force of gravity assists in retaining the cross bar member 106 in the slot. As shown in FIG. 4, the slots 116 include an inset 118, into which the cross bar 106 fits to provide additional stability and security to the cross bar support system 100. Alternative embodiments include, for example, a slot initially disposed substantially horizontally which connects to a downwardly-cut inset 118. The downwardly-cut inset 118 may be angled downward at any angle.

Each slot 116 includes parallel flat sides spaced apart to snugly to accommodate the cross bar 106. Thus, each slot 116 is appropriately sized so that the cross bar member 106 can slide into the slot but is not allowed to rotate within the slot. For example, if the cross bar member is a 12.5 mm square, then the slot is approximately 12.6 mm wide, to accommodate some slight variation in the size of the cross bar member, but to avoid any excess freedom of movement.

The cross bar assembly 102 further includes at least one clamping device 120 for retaining the cross bar on the support member 104. In one embodiment, the clamping device 120 is a compression clamp, by which the handle 122 may be turned to threadingly actuate the clamping device to firmly hold the cross bar 106 to one of the support members 104a or 104b.

In the embodiment shown in FIG. 4, the cross bar assembly 102 utilizes the clamp 120 to hold the cross bar 106 to the support member 104a. As shown in FIG. 4, the cross bar 106 is not clamped to the second vertical support member, the vertical support member 104b. In an alternative embodiment, the cross bar 106 may be clamped to the other support member, 104b. The cross bar assembly 102, when utilizing the clamp 120 to hold the cross bar 106 to the support member 104a (for example) need not be clamped to the second vertical support member 104b.

An embodiment of the cross bar 106 not having a second clamp allows the cross bar to be repositioned by a single surgical assistant working from one side of the surgical support platform 108. This arrangement provides additional flexibility to the use of the cross bar support system 100.

In the above single-clamp embodiment, the non-clamped end of the cross bar 106 is horizontally retained in the slot 116 by an enlarged head (not shown) disposed on the end of the cross bar 106. Thus, the enlarged head on the end of the cross bar 106 which extends through the vertical support member 104b to the outer side of the member 104b, is on the opposite end of the cross bar 106 from the claim 120.

Alternatively, within the scope of the invention, the cross bar 106 may include a second clamping device 120 for holding the cross bar 106 to the support member 104b, if such is deemed necessary to provide additional stability to the cross bar support system 100.

In a second embodiment of the cross bar support system, each of the pair of vertically extending support members is a conventional retractor support apparatus such as that shown in FIGS. 1 and 2. In this second embodiment, the cross bar is not a single bar extending across the patient support platform 108, but includes an extension bar and clamping devices by which the extension is attached to the horizontally extensions of the vertical supports. An example of such an embodiment is shown in FIG. 5.

As shown in FIG. 5, an alternate embodiment of a cross bar support system 140 includes two vertically extending members 142a and 142b, both of which include horizontal extensions 144.

In FIG. 5 is shown a cross bar support system 140 including a cross bar assembly 146. The cross bar assembly 146 shown in FIG. 5 includes two horizontal extensions 144, an extender bar 148, and two dual clamps 150. In FIG. 5, no ratcheting lifting devices 24 are shown, but any number may be mounted on the cross bar assembly 146, as needed for a given surgical procedure, and limited only by the space available on the cross bar assembly 146. The ratcheting lifting devices 24 may be mounted on any or all of the horizontal extensions 144 and the extender bar 148.

The preferred ratcheting lifting devices 24 are the same as those shown in FIGS. 1 and 2, which are commercially available from RULTRACT, INC., Cleveland, Ohio. Of course, other equivalent ratcheting lifting devices may be substituted for the RULTRACT® devices, if such equivalent devices are capable of being mounted on the cross bar assembly 146 as described herein. The ratcheting lifting device 24 may be attached for retraction either to a retractor assembly, such as a rake plate with a plurality of rakes or to a single retractor rake, as shown in FIG. 4 for the first embodiment of the cross bar support system 100.

As mentioned above, the cross bar support system 140 includes a pair of vertical support members 142. As shown in FIG. 5, the horizontal extensions 144 are integrally attached to and supported by the pair of vertically extending support members 142. In alternative embodiments the horizontal extensions 144 may be separate parts, appropriately attached to the vertically extending supports 142a and 142b. The horizontal extensions 144 extend horizontally outward above a patient support platform (not shown in FIG. 5, but similar to the patient support platform 108 shown in FIG. 4). The vertical support members 142 are essentially identical to each other. In one embodiment of the vertical support member, each member 142 comprises a lower portion 152 and an upper section 154, connected by a coupling 156. The coupling 156 couples by means of a key and lock arrangement more fully described below, in which the sections interlock to provide a secure attachment of the lower portion 152 and the upper portion 154. In this embodiment, all upper portions 154 are identical and all lower portions 152 are identical, as a result of which each can be mounted on either side of the patient support 108. In one embodiment the coupling 156 is a splined coupling as described in greater detail below.

As shown in the embodiment of FIG. 5, each vertical support member 142 includes an outwardly extending portion 110 similar to the outwardly extending portion 110 shown in FIG. 4 and described above. In the support apparatus shown in FIG. 5, the outwardly extending portion 110 is in the lower portion 152 so as to allow additional space in the surgical field near the patient. The outwardly extending portion 110 includes the bends 38 and 40 and the bends 112 and 114. Thus, the coupling 156 of the vertically extending member 142 is approximately vertically above the part of the lower portion 152 adjacent an attachment clamp 157. The outwardly extending portion 110 adds stability to the support members 142.

In an alternate embodiment, the vertical support members may include no additional bends 112 and 114, so that the outwardly extending portion of both the upper section 154 and the lower portion 152, and the coupling 156, remain further outboard for the entire vertical height of the vertical support members 142. In another alternate embodiment, the vertical support members include no outwardly extending portion, so that there are no bends such as the bends 38, 40, 112 and 114 of the described embodiment. Other combinations may be possible as well.

The support members 142 are releasably attachable by the attachment clamp 157 to the patient support platform (not shown in FIG. 5), such as an operating table. The attachment clamp 157 is shown in FIG. 5 as a standard compression clamp for attachment to a rail disposed on most patient support platforms. The clamp may generally be any conventional attachment device, as would be used for clamping vertical support bars and other surgical equipment to the patient support platform.

As is apparent from FIG. 5, the cross bar support system 140 is quite stable, primarily due to the firm attachment to the patient support platform and the attachment through the horizontal extensions 144, the extender bar 148 and the two couplings 150, connecting together with the support members 142 to form a unitary assembly. Accordingly, it is not necessary that the support members be attached to the platform 108 by a device which restricts the rotation of the support members, such as the splined coupling which will be described below in relation to another embodiment of the present invention. However, having the horizontal supports 144 aligned by means of a rotation-restricting device will simplify setting up the cross bar assembly 146.

In one embodiment, the horizontal extensions 144 and the extender bar 148 are made from metal stock which is square in cross-section. In one embodiment, the stock is about ½ inch by ½ inch square (about 12.5 mm×12.5 mm). In coordination with this embodiment, both the clamps 150 and the ratcheting lifting devices 24 include a square opening of appropriately matching size so that the clamps 150 and the devices 24 can be easily and reliably mounted on the horizontal extensions 144 and the extender bar 148. Thus, for example, both the opening in the clamp 150 and the opening in the device 24 may be approximately 12.6 mm square, to accommodate some slight variation in the size of the cross bar member, but to avoid any excess freedom of movement. It is noted that while the stock is square in this embodiment, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

Figure 6:
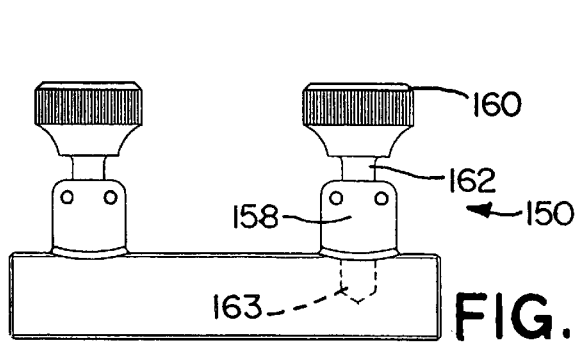
FIG. 6 is a side elevational view of a coupling device for use in the embodiment illustrated in FIG. 5.

The coupling 150 is shown in more detail in FIG. 6. The coupling 150 includes a pair of locking devices 158 actuated by a handle 160. As shown in FIG. 6, the locking devices 158 are threadingly actuated, such that appropriately rotating the handle 160 extends or withdraws a shaft 162 thereby pressing a shaft tip 163 (shown in phantom in FIG. 6) against a bar inserted into the coupling, resulting in securely positioning the bar in the coupling, or in releasing the bar. In this embodiment the shaft tip 163 is tapered and sized to fit into a bor 164 as shown in FIG. 7A.

Figure 7B:
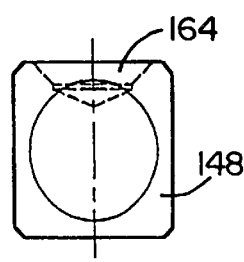
FIG. 7B is a cross-sectional view taken at line B—B of FIG. 7A.
Figure 7A:
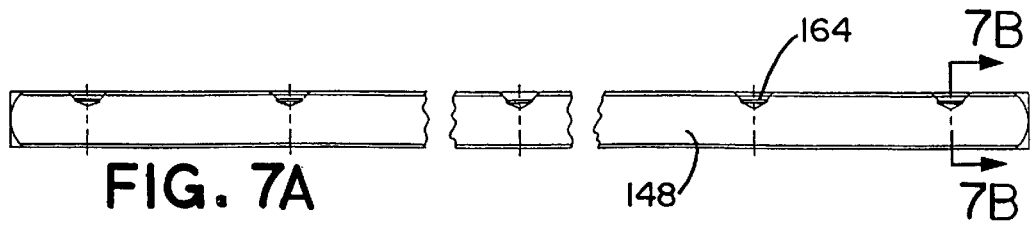
FIG. 7A is a side elevational view of an extension bar for use in the embodiment illustrated in FIG. 5.

The extender bar 148 is shown in FIGS. 7A and 7B. The extension bar 148 is appropriately dimensioned in the length and cross-sectional dimensions to coordinate with the horizontal extensions 144 of the vertical supports 142 when the supports are mounted on a standard patient support platform. Of course, various lengths of the extender bar 148 may be made available to make it possible to use the cross bar assembly on various widths of patient support platform. As shown in FIGS. 7A and 7B, the extension bar includes the regularly spaced bores 164, similar to the bores 48 shown in FIGS. 1 and 2. Similarly, the horizontal extensions 144 include such regularly spaced bores 164.

FIG. 7B, which is a cross-sectional view taken at line B—B of FIG. 7A, shows a cross section of such a bore 164. As shown, the locking device 158 on the coupling 150 includes the lower end 163 on its threaded shaft 162 appropriately sized and configured to fit into each of the bores 164.

The cross bar assembly 146 is assembled by inserting the horizontal extensions 144 into one side of the couplings 150, and inserting the extension bar 144 into the other end of each coupling 150, and tightening the pair of locking devices 158 on the couplings, such that the shaft tip 163 of the shaft 162 is inserted into one of the bores 164. The cross bar assembly 146 is thereby assembled to form the cross bar support system 140.

Figure 8:
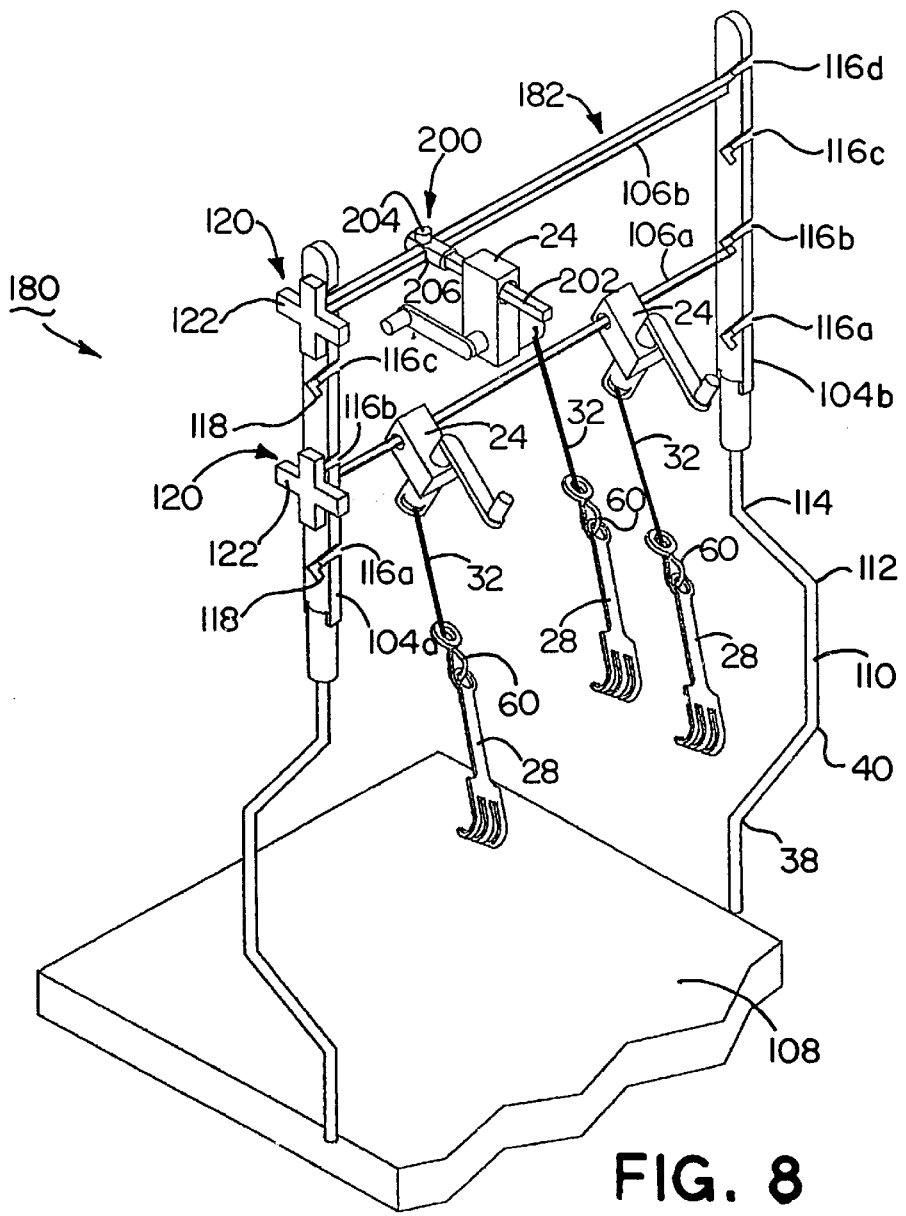
FIG. 8 is a perspective view of a second cross bar support assembly in accordance with the first embodiment of the present invention.

Referring now to FIG. 8, an embodiment of the present invention in the form of a cross bar support system 180 is shown, which includes a cross bar assembly 182 having a first cross bar 106a and a second cross bar, 106b. The second cross bar 106b is attached to and supported by the pair of vertically extending support members in the same manner as described for the cross bar 106 shown in FIG. 4. The second cross bar 106b may be mounted either above or below the first cross bar 106a, and may be mounted in any available pair of the plurality of slots 116a, 116b, 116c and 116d on the vertical support members 104a and 104b.

In the cross bar assembly 182 shown in FIG. 8, the second cross bar 106b may have mounted thereon one or more ratcheting lifting devices 24. Although FIG. 8 shows a ratcheting lifting device 24 mounted on an extender bar 148 rather than directly on the second cross bar 106b, such a device 24 would be mounted thereon in the same manner as described above with respect to the ratcheting lifting devices 24 mounted on the cross bar assembly 200 shown in FIG. 4.

As shown in FIG. 8, the cross bar assembly 182 may include a horizontally extending extension 200, upon which a ratcheting lifting device 24 may be disposed. Although not shown in FIG. 8, more than one extension 200 may be mounted on either the first cross bar 106a or the second cross bar 106b. Similarly, an extension 200 may be mounted on the cross bar 106 of the cross bar assembly 102 shown in FIG. 4.

As described in more detail below with respect to FIG. 9, the extension 200 mounted on the second cross bar 106b includes an extender bar portion 202, a clamp 204, and a first receptacle 206 for receiving the cross bar 106b of the cross bar assembly 182, in this example.

As shown in FIG. 8, the extension 200 extends at a right angle to the cross bar. However, other angles are possible where such is helpful to provide flexibility in the angle at which the retractor apparatus is suspended with respect to the patient. Such other angles are within the scope and contemplation of the present invention. In such an embodiment, the first receptacle 206 is at an angle other than a right angle to the longitudinal direction of the extender bar portion 204.

Referring to FIG. 8, the cross bar assembly 182 utilizes the clamps 120 to hold the cross bars 106a and 106b to the support member 104a (for example). As described above for the embodiment shown in FIG. 4, the cross bars 106a and 106b are not clamped to the second vertical support member 104b. Alternatively, either or both of the cross bars 106a and 106b may be clamped to the other support member, 104b. The embodiment of the cross bar 106a and/or 106b which is not provided with a second clamp allows the cross bar to be repositioned by a single surgical assistant from one side of the surgical support platform 108, thus providing additional flexibility to the use of the cross bar support system 180. In this embodiment, the non-clamped end of the cross bar 106a and/or 106b is horizontally retained in the slot 116 by an enlarged head (not shown) located on the end of the cross bar 106 extending through the vertical support member 104b to the outer side of the member 104b. Alternatively, within the scope of the invention, either or both cross bar 106a and 106b may include a second clamping device 120 for holding the cross bar to the support member 104b, if such is deemed necessary to obtain additional stability to the cross bar support system 180.

The second cross bar 106b, like the first cross bar 106a, may include a plurality of further ratcheting lifting devices 24, mounted on either of the cross bars, or upon one or more extension bars 200 mounted on either of the cross bars. It is noted that additional cross bars 106 may be mounted on the cross bar assembly 200 or 180, limited only by the number of slots 116. In turn, the number of slots 116 is limited only by the length of the vertical extension 104 and considerations of strength and utility.

The following describes various methods by which the cross bar may be put to use in a surgical procedure. The steps are generally outlined, and are not intended to limit the many uses to which the invention may be put.

In one embodiment, the present invention is a method of providing surgical retraction to a patient positioned relative to a support platform, including the steps of: (1) mounting a pair of vertically extending support members with respect to the platform; (2) mounting a cross bar to the pair of vertically extending support members; (3) mounting a lifting device on the cross bar; and (4) applying retraction to the patient. In one embodiment, the step of mounting a lifting device further includes attaching the lifting device to a retractor assembly. In one embodiment, the step of mounting a lifting device further includes attaching the retractor assembly to an anatomical part of the patient. In one embodiment, the method includes mounting a second cross bar to the pair of vertically extending support members, and may further include mounting a lifting device on the second cross bar for applying additional retraction to the patient.

Figure 9:
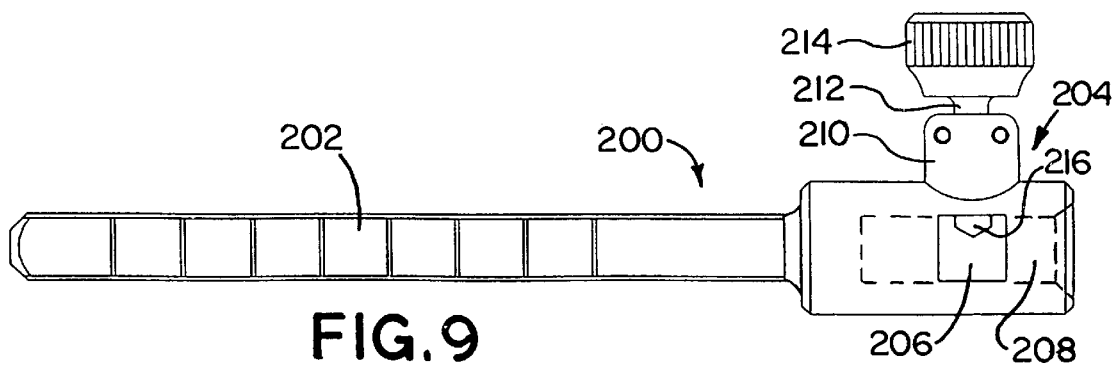
FIG. 9 is a side elevational view of a "head to toe" extender in accordance with an embodiment of the present invention.

The second embodiment of the present invention, shown in FIG. 9, is a right-angled extension bar 200 for a retractor support system. The horizontal extension of a vertically extending support, such as the horizontal extension 144 shown in FIG. 5, normally extends outward in a direction transversely across the patient's body. When the right-angled extension bar 200 of the present invention is attached to the horizontal extension 144, the extension bar 200 is oriented parallel with the patient's body, i.e., in a head to toe direction. Accordingly, the right-angled extension bar 200 of the present invention has been referred to as a "head to toe" extension. As a result of the head to toe extension 200, the surgeon is provided with a further novel and improved adaptability in configuring the retractor support system. Thereby, the surgeon may better adapt to the changing conditions and needs of the patient during surgery.

The head to toe extension 200 extends from a device for mounting a ratcheting lifting device 24 or other surgical devices which can be mounted on such bars as have been disclosed in the foregoing descriptions of the embodiments of the invention. The head to toe extension 200 has a ratcheting lifting device 24 or other devices mounted thereon.

As shown in FIG. 9, the head-to-toe extension 200 includes a bar portion 202, a clamp 204, a first receptacle 206, and a second receptacle 208. Both the first receptacle 206 and the second receptacle 208 are configured for receiving a horizontal support bar, such as that shown in FIGS. 1, 2 or 5, from the vertically extending support device 36 or 142, respectively. As shown in FIG. 9, the first receptacle 206 is disposed to receive the horizontal support bar at a right angle to the longitudinal axis of the head to toe extension. The first receptacle 206 is similarly sized and dimensioned to receive the cross bar 106 or the cross bars 106a or 106b.

As is shown in FIG. 9, the second receptacle 208 is disposed to receive the horizontal support bar collinearly with the longitudinal axis of the bar 202, and thus to act as a simple extension of the horizontal support.

The clamp 204 includes a clamp body 210, a threaded shaft 212, and a handle 214. As shown in FIG. 9, the lower end (opposite the handle) of the shaft 212 is configured to securely fit into a positioning bore such as the bore 164 shown in FIGS. 7A and 7B. The clamp 204, as shown in FIG. 9, is advantageously positioned to retain the horizontal bar in either the first receptacle 206 or the second receptacle 208. A shaft tip 216 on the threaded shaft 212 interacts with the bores 164 to retain the horizontal bar in the clamp 204. It will be noted that while the horizontal bar can only be inserted a short distance into the second receptacle 208, the horizontal bar can be inserted any desired distance into the first receptacle 206, since the first receptacle 206 is an opening which passes completely through the clamp 204.

In one embodiment, a cross section of the bar 202 is rectilinear. In another embodiment, the bar 202 is square. The bar 202 should be the same size as the horizontal extending portions 44 and 144 and the cross bars 106, 106a and 106b, described with respect to the other embodiments of the present invention.

The following describes various methods by which the extension may be put to use in a surgical procedure. The steps are generally outlined, and are not intended to limit the many uses to which the invention may be put.

In one embodiment, the present invention includes a method of providing surgical retraction to a patient, a portion of which is positioned relative to a support platform, including the steps of: (1) mounting with respect to the support platform a generally vertically extending support member; (2) mounting with respect to the vertically extending support member an extension, the extension including an extender bar; (3) mounting a lifting device on the extender bar; and (4) applying retraction to the patient. In one embodiment, the extension includes a receptacle and the step of mounting the extension includes placing a portion of the vertically extending support member into the receptacle. In one embodiment, the extension includes a clamp disposed in relation to the receptacle and the step of mounting the extension includes retaining the portion in the receptacle with the clamp. In one embodiment, the receptacle is disposed to receive the portion at approximately right angles to the extender bar. In one embodiment, the vertical support member has a horizontally extending portion, and the step of mounting the extension includes mounting the extension on the horizontally extending portion.

Figure 10:
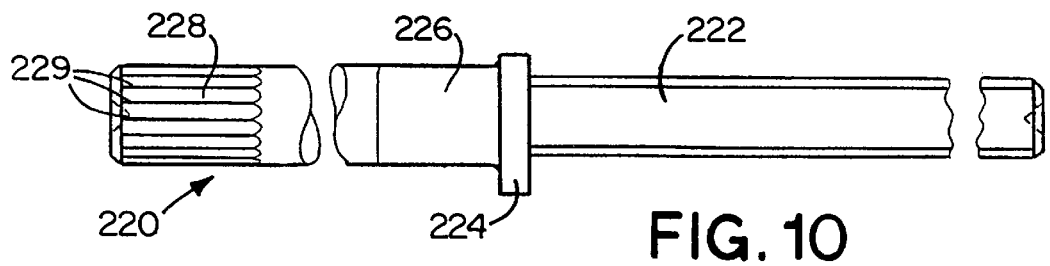
FIG. 10 is a side elevational view of an embodiment of a support pole having a splined segment and a square segment.

The third embodiment of the present invention is generally illustrated in FIGS. 10–14. As shown in FIG. 10, this embodiment includes a lower portion 220 for a vertical support member for a retractor support system. The lower section 220 includes a base segment 222, a radially extending shoulder 224, a main segment 226, and a splined segment 228.

In one embodiment, the lower section 220 is machined from a single piece of stock, but may also be made by welding together appropriately sized and shaped pieces. In one embodiment, the base segment 222 is generally square in cross-section, and is appropriately sized and adapted to fit into an anchoring receptacle having a standard compression fitting and a standard device for clamping attachment to a patient support platform such as an operating table (not shown). In a standard device, a clamp, such as the device 166 shown in FIG. 5, may be integrally formed on the base segment 222 for attachment to a standard-sized bar or rail extending from the side of the patient support. The device may alternately include a standard compression fitting having a square opening for receiving the base segment of items such as IV holders and other equipment which may be used during a surgical procedure. The base segment 222 of the lower section 220 is sized appropriately to fit into the square opening of the standard compression fitting. The base segment 222 may have any desired length, and in one embodiment is at least about one foot (30 cm) in length, to allow for an adequate range of vertical adjustment of the vertical support member.

The base segment 222 abuts a radially extending shoulder 224, which effectively establishes a minimum height at which the vertical support can be mounted. The base segment 222 may be raised and clamped into position by the compression fitting, but it cannot be lowered any further than allowed by the shoulder 224.

The portion of the lower section 220 above the shoulder 224 is the main segment 226. The main segment 226 may have any cross-sectional shape, but in one embodiment is round in cross-section. The main segment 226 in one embodiment is in the range from about 1 to about 2 feet in length (about 30 cm to about 60 cm), but it may be longer or shorter as required for a particular application. The main segment may be machined from stock having a diameter in the range from about ½ inch to about ⅝ inch (about 12 mm to about 25 mm). In one embodiment, the radially extending shoulder 224 has a slightly larger diameter than the main segment 226, but may have the same diameter, as long as the diameter or width of the shoulder 224 is larger than the width of the opposite sides of the square base segment 222.

The main segment 226 includes the splined segment 228. The splined segment 228 has a plurality of teeth 229. In one embodiment, the splined segment 228 has at least 12 teeth 229, and in one embodiment, the splined segment has 19 such teeth. In one embodiment, the splined segment 228 is machined from the same stock from which the main segment 226 is made. Therefore, the teeth 229 of the splined segment will normally extend radially outward no further than the diameter of the main segment 226.

Figure 11:
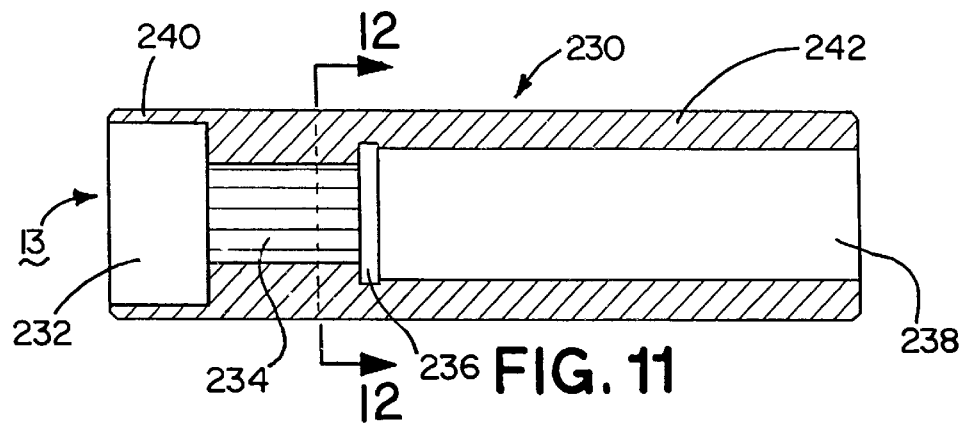
FIG. 11 is an longitudinal cross-sectional view, taken at line 11—11 of FIG. 13 of a coupling device including a coupling spined segment.
Figure 12:
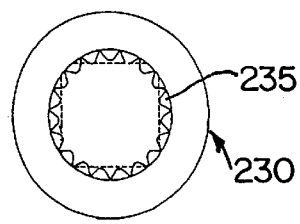
FIG. 12 is an axial cross-sectional view taken at line 12—12 of the coupling device shown in FIG. 11.
Figure 13:
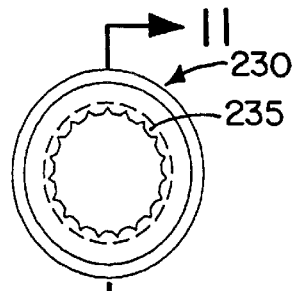
FIG. 13 is an axial elevational view of the coupling device of FIG. 11 taken from position 13 in FIG. 11.

As shown in FIGS. 11, 12 and 13, this embodiment includes a splined coupling 230. FIG. 11 is a longitudinal cross-sectional view, taken at line 11—11 of the splined coupling 230 shown in FIG. 13. FIG. 12 is an axial cross-sectional view, taken at line 11—11 of the splined coupling shown in FIG. 11, and FIG. 13 is an axial elevational view of the coupling device of FIG. 11 taken from position 13 in FIG. 11. The splined coupling 230 is adapted to receive the splined segment 228 of the lower portion 220.

The splined coupling 230 includes a shallow recess 232, a coupling splined segment 234, a plurality of splines 235, a stop plug 236, and a deep recess 238. The shallow recess 232 is formed by a wall 240. The deep recess 238 is formed by the wall 242. In use, the splined segment 228 of the lower section 220 is inserted into the shallow recess 232, and the splined segment 228 is received by the coupling splined segment 234 in an interlocking, relatively tight fit. The splines 235 of the coupling splined segment 234 are machined to match in number and size the splines 229 on the splined segment 228 of the lower section 220. When the respective splined segments 228 and 234 are interlocked, the coupling 230 cannot be rotated with respect to the lower section 220.

Figure 14:
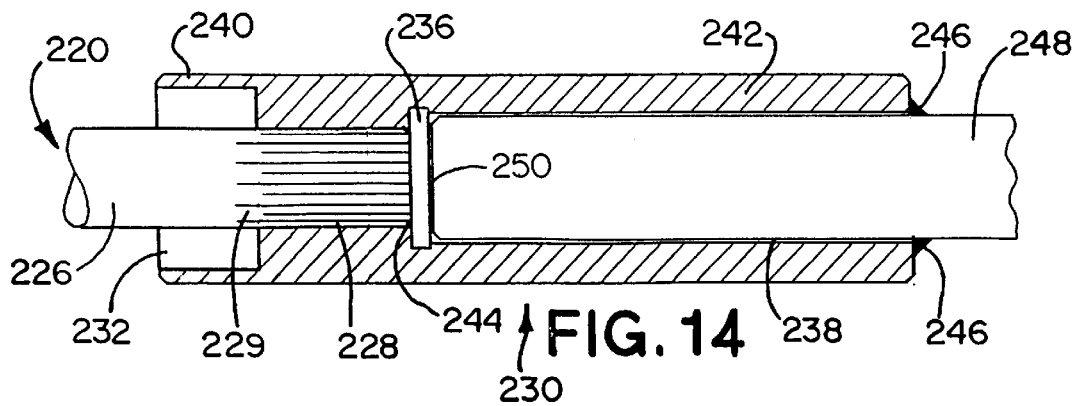
FIG. 14 is a longitudinal cross-sectional view of a splined coupling with a splined lower segment inserted and an upper segment welded in place.

As best shown in FIG. 14, when the splined segments are fully interlocked, the lower section end 244 comes in contact with and is stopped by the stop plug 236. The stop plug 236 acts to prevent over-insertion of the lower segment into the splined coupling 230. When the splined segments 228 and 234 are interlocked, the wall 240 of the shallow recess 232 acts as a skirt to cover a small portion of the lower section near the splined segment 228. The skirting effect of the wall 240 helps to avoid entry of contaminants into parts of the coupling such as the splined segment 234, which would be difficult to clean and sterilize.

The number of splines in the two splined segments should match so that the maximum number of possible interlocking positions are enabled. In one embodiment, different numbers of splines may successfully interlock, for example 24 splines mating with, e.g., 12 splines. In one embodiment, in both the splined segment 228 of the lower section, and in the coupling splined segment 234 of the coupling 230, there are at least 12 splines. In one embodiment, in each splined segment there are 19 splines. In this embodiment, the 19 splines result in 18 possible alignments of the two splined segments.

These 18 possible alignments of the lower portion and the upper portion of the vertically extending support provide a wide range of possible positions from which the surgeon can select to position the ratcheting lifting device 24. This advantage is particularly suitable and helpful for the less-invasive mid-cab procedure. As discussed above, the variability in position of the internal mammary artery requires great flexibility on the part of the surgeon in access that artery for dissection and harvest. Thus, the surgeon is provided with a surgical support apparatus for a ratcheting lifting device with which the angle of retraction can be closely controlled over a very wide range. Since the splined connection is maintained by the interlocking of the splines and the force of gravity alone, it is quite easy for the surgeon or a surgical assistant to change the angle of the upper section of the vertically extending support during the course of a surgical procedure. By means of the splined coupling, by which the exact angle at which the retraction apparatus is suspended with respect to the patient's body may be selected and reliably retained without the possibility of slippage. The splined coupling allows for adjustment of the angle during the course of a surgical procedure, thereby allowing the surgeon to better adapt to the changing conditions and needs of the patient.

Referring again to FIG. 14, in the embodiment of the present invention, the splined coupling 230 may be attached by a weld 246 to an upper section 248 (partially shown in FIG. 14). The weld 246 should be smooth and continuous around the circumference of the upper section 248 and the coupling 230, and should be free of seams, cracks, pinholes or other openings into which contaminants could become lodged. As shown in FIG. 14, the upper section 248 extends fully into the deep recess 238, and the lower end 250 of the upper section 248 is in contact with the stop plug 236 when the weld 246 is made.

In the upper section 248 of the present embodiment, above the weld 246, is essentially identical to the upper section 154 described in reference to FIG. 5. The description of the upper section 154 applies equally to the upper section 248. Thus, the upper section 248 includes horizontal extensions which are made from metal stock which is square in cross-section. In one embodiment, the stock is about ½ inch by ½ inch square (about 12.5 mm×12.5 mm). In coordination therewith, each device mounted thereon, such as the clamps 150 and the ratcheting lifting devices 24, include a square opening of appropriately matching size so that such clamps and the devices 24 can be easily and reliably mounted on the horizontal extensions of the present invention. Thus, for example, as described with reference to the clamp 150 and the device 24, the opening in any device used on the horizontal extension of the upper section of the present embodiment may be approximately 12.6 mm square, to accommodate some slight variation in the size of the cross bar member, but to avoid any excess freedom of movement. It is noted that while the stock is square in this embodiment, other configurations may be used, such as triangular, pentagonal, hexagonal, or rectangular for example. Furthermore, when a term such as "square" is used, this refers to the overall cross-sectional shape, rather than to a perfectly square (or other) cross-section. Thus, a square stock may have slightly rounded corners, for example, and still be considered square.

In one embodiment, the splines 229 and 235 on the respective splined segments 228 and 234 are involute. In the embodiment shown in FIG. 10, the key-like splined portion 228 is disposed on the upwardly-directed end of the lower portion of the support member. Alternatively, the key-like splined segment may be disposed on the downwardly-directed upper portion of the support member, although such an embodiment would not provide the contamination-avoiding benefit of the downwardly-oriented skirt formed by the wall 240 and the recess 232.

The following describes various methods by which the splined connection may be put to use in a surgical procedure. The steps are generally outlined, and are not intended to limit the many uses to which the invention may be put.

In one embodiment, the present invention includes a method of providing surgical retraction to a patient positioned relative to a support platform, including the steps of: (1) mounting upper and lower portions of a support member with respect to each other by a lock-and-key-like splined connection and with respect to the platform; (2) positioning a lifting device above the patient by mounting the lifting device with respect to the upper portion of the support member; and (3) applying retraction to the patient. In one embodiment, the lock-and-key-like splined connection includes a key-like splined portion and a lock-like splined portion whereby the upper portion and the lower portion may be matingly interconnected. In one embodiment, the upper portion further includes a horizontally extending portion. In one embodiment, the step of mounting further includes selecting a desired angle of orientation between the horizontally extending portion and the support platform. In one embodiment, the step of mounting further includes mounting the upper portion to the lower portion by matingly interconnecting the key-like splined portion to the lock-like spined portion at the desired angle. In one embodiment, the step of mounting further includes attaching the lower portion to an anchoring receptacle on the support platform.

In one embodiment, the present invention relates to a method of providing surgical retraction to a patient positioned relative to a support platform, including the steps of: (1) positioning a lifting device above the patient, said positioning including mounting the lifting device by a multiple part generally vertically extending support member which has a lock-and-key-like splined connection between at least two of the multiple parts; and (2) adjusting the position of the lifting device relative to the patient by selecting an angular relation between a first one of the parts and a second one of the parts at the lock-and-key-like splined connection; and (3) applying retraction to the patient.

In one embodiment, the present invention includes a method of mounting a surgical retractor with respect to a patient support platform, including the steps of: (1) mounting with respect to the platform a vertically extending support member which has a lower portion, an upper portion, and a lock-and-key-like splined connection for connecting the lower portion to the upper portion; (2) connecting the lower portion to the upper portion by inserting a key-like splined portion into a lock-like splined portion; and (3) mounting the surgical retractor on the vertically extending support member. In one embodiment, the upper portion further includes a horizontally extending portion. In one embodiment, the step of connecting further includes selecting a desired angle of orientation between the horizontally extending portion and the patient. In one embodiment, the step of connecting further includes mounting the upper portion to the lower portion by matingly interconnecting the key-like splined portion to the lock-like spined portion at the desired angle. In one embodiment, the step of mounting further includes attaching the lower portion to an anchoring receptacle on the support platform.

Another embodiment of the present invention, shown in FIGS. 15–17 and 19–20, is a low profile support member 300 for a surgical retraction apparatus, such as the RUL-TRACT® retractor. The low profile support member 300 includes a lower portion 110 having an attachment means, for example the attachment clamp 157 shown in FIG. 5, which is adapted for mounting to a support platform 108, an upper portion 310 having a bend portion 312, a first horizontal extension 314, and a splined coupling adaptor 316 for connecting together the lower portion 110 and the upper portion 310. The horizontal extension may include a square cross section portion or segment 318. The splined coupling adaptor 316 includes a splined segment having a key-like splined portion and a lock-like splined portion, as described above, and thus may be referred to as a lock-and-key-like splined connection, as described above. The splined portions are generally similar to those described above with respect to the embodiments of FIGS. 10–14, except as noted in the description below.

FIGS. 15–17 show various embodiments of the low profile support member 300 of the present invention, while FIG. 18 shows an embodiment of the support member described above with respect to FIGS. 10–14, which may be considered a "standard profile" support member 260 for comparative purposes with the low profile support member 300.

FIG. 15 is a perspective view of one embodiment of the low profile support member 300, including a lower portion 110, an upper portion 310, and an extender portion 320 with a lifting device 24 mounted on the extender portion 320. The extender portion 320 is mounted on and attached to the upper portion 310 by a clamp 321. The embodiment shown in FIG. 15 includes the lower portion 220 as described above with respect to FIG. 10, and a single rake 28 attached to a pivot hub connector 34 via a snap ring 60, as described above with respect to FIGS. 2, 3A and 3B, and the lifting device 24 described with respect to FIG. 1. In the embodiment of the low profile support member 300 shown in FIG. 15, the lower portion 110 is connected to the upper portion 310 by a splined coupling segment 316.

FIG. 16 is a perspective view of another embodiment of the low profile support member 300 of the present invention, including the lower portion 110, the upper portion 310, and the extender portion 320 with a lifting device 24 mounted on the extender portion 320. The extender portion 320 is mounted on and attached to the upper portion 310 by the clamp 321. The embodiment shown in FIG. 16 includes the lower portion 110 as described above with respect to FIG. 4, and the lifting device 24, the rake plate 26 and the rakes 28 associated therewith, as described above with respect to FIG. 1. In the embodiment of the low profile support member 300 shown in FIG. 16, the lower portion 110 is connected to the upper portion 310 by the splined coupling segment 316.

FIG. 17 is a perspective view of another embodiment of the low profile support member 300 of the present invention, including a lower portion 110, the upper portion 310, and the extender portion 320 with a lifting device 24 mounted on an extender bar 148, which is in turn mounted on the extender portion 320. The extender portion 320 is mounted on and attached to the upper portion 310 by the clamp 321. The embodiment shown in FIG. 17 includes the lower portion 110 as described above with respect to FIG. 4, the extender bar 148 as described above with respect to FIG. 9, and the lifting device 24, the rake plate 26 and the rakes 28 associated therewith, as described above with respect to FIG. 1. In the embodiment of the low profile support member 300 shown in FIG. 17, the lower portion 110 is connected to the upper portion 310 by the splined coupling segment 316.

FIG. 18 is a perspective view of an embodiment of a "standard profile" support member 260 of the present invention, such as has been described above with respect to FIGS. 10–14. The embodiment of the standard profile support member 260 shown in FIG. 18 includes the extender bar 148, which is mounted on a horizontally extending portion 262 of the upper section 248. No lifting device is shown with respect to the embodiment shown in FIG. 20, but any lifting device, e.g., the lifting device 24, and/or other apparatus such as an extender bar, for example, the extender bar 148, may be used therewith.

As is apparent from the comparison of FIGS. 15–17 with FIG. 18, the low profile support member 300 extends vertically from a position above the patient, rather than from a position near the side the patient at the side of the support platform 108 as in the standard profile support member 260. In other words, as shown in FIGS. 15–17, the low profile support member 300 has a substantial portion of its vertical extension shifted from a position at the side of the support platform 108 to a position laterally inward from the side, over the center of the support platform 108. Using as an example a supine patient lying on the surgical support platform 108, a patient midline plane may be defined by the head-to-toe midline of the patient, that is, by a line generally aligned with and located along the patient's spine. In the low profile support member of the present invention, the vertical extension of the support member is at or near, i.e., substantially aligned with, the patient midline plane. This change in position of the vertical extension provides additional flexibility to the surgeon in selecting the exact angle and direction from which retraction is to be applied to the patient. As used herein, the term "substantially aligned with the patient midline plane" includes arrangements in which the vertical extension is off the plane but is within a few inches of the patient midline plane, i.e., between the patient's shoulders. Such arrangements provide substantially the same benefits as an arrangement in which the vertical extension is in the patient midline plane, and are within the scope of the present invention.

Another important benefit provided by the low profile support member of the present invention, as shown in FIGS. 15–17, is the provision of a significant amount of additional space in the area of the surgical field occupied by surgical personnel, specifically in the area at the side of the surgical support platform 108, at the side of the surgical patient. Thus, the surgical team is provided with additional "elbow room" in which to work during the surgical procedure.

In addition, as may be observed by comparison of FIGS. 15–17 with FIG. 18, the standard profile support member 260 shown in FIG. 18 has a significantly higher profile than the low profile support members 300 shown in FIGS. 15–17, when the horizontally extending portions are compared. Thus, the present invention provides a greater range of heights from which the lifting apparatus can be used.

Figure 19:
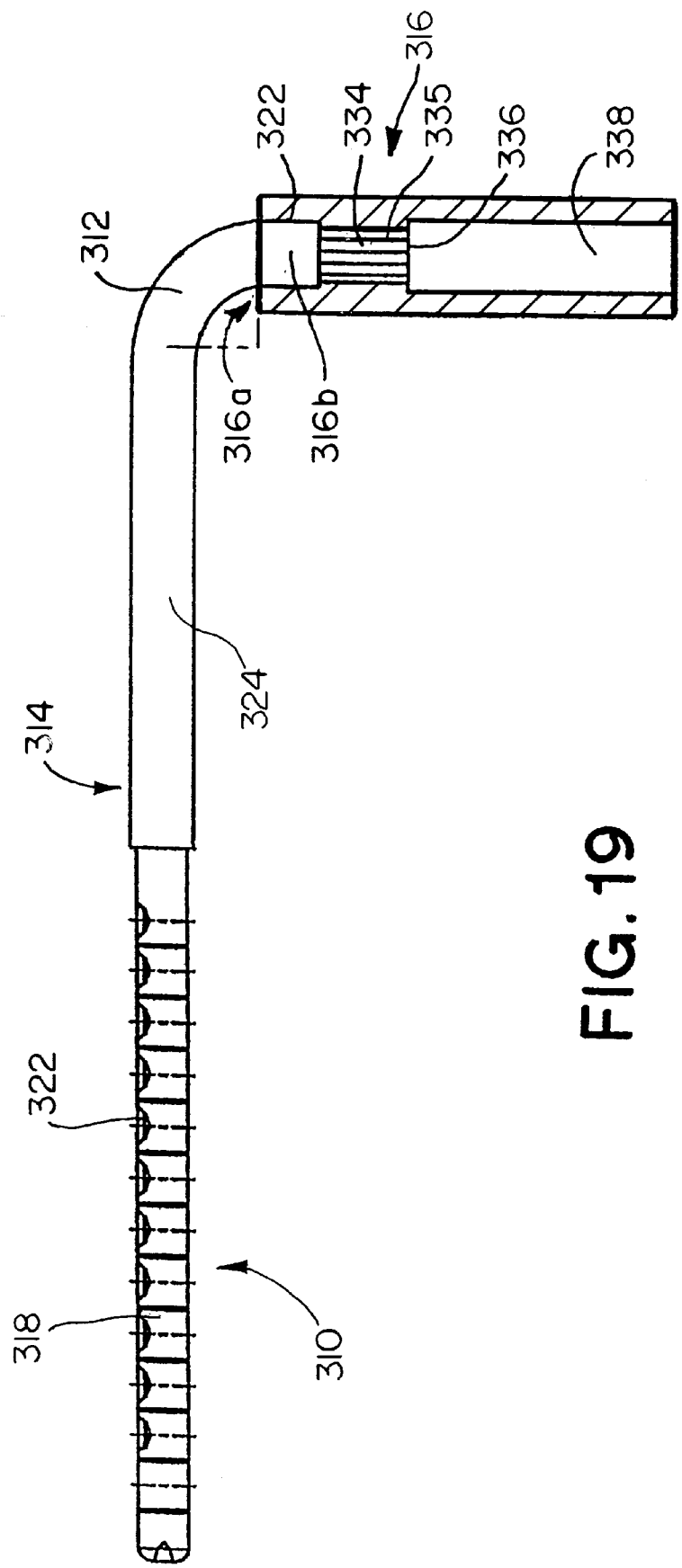
FIG. 19 is a side elevational view of an embodiment of a low profile support member having a splined segment and a square segment.

FIG. 19 is a side elevational view providing a more detailed view of an embodiment of an upper portion 310 of a low profile support member 300. The upper portion 310 shown in FIG. 19 includes a bend segment 312, a first horizontal extension 314 and the splined coupling segment 316. The upper portion 310 is generally similar to the support members described elsewhere in the present specification. The bend segment 312 forms a transition from a vertical to a horizontal alignment. The horizontal extension 314 includes a square segment 318 which continues the generally horizontal extension of the first horizontal extension 314, upon which a device such as the lifting device 24, the extension bar 148, or the extender portion 320 may be mounted. The lower portion 110 of the low profile support member 300 may be essentially the same as the lower portion 110 described above in greater with respect to the embodiments of FIGS. 4 and 8.

The bend segment 312, in the embodiment shown in FIG. 19, forms a 90° angle between the vertically oriented splined coupling segment 316 and the first horizontal extension 314. This angle may be varied, and may include combinations of angular connections. In one embodiment, the radius of the bend is about two inches, although other radii may be used. The bend segment 312, in the embodiment shown in FIG. 19, has been bent subsequent to machining of the remainder of the low profile support member 300, but in another embodiment may be bent prior to machining. In one embodiment, the bend segment 312 is not actually a bend in a single piece of stock material, but instead is made by attaching two separate pieces of stock material, such as by welding, bolting or otherwise attaching together the pieces.

In a surgical retractor using a low profile support member 300, such as those described herein, for example, the first horizontal extension 314 of the low profile support member 300 is directly connected at a socket 316a in the splined coupling adapter 316 by a base portion 316b with relatively minimal vertical rise compared to the relatively greater vertical rise of the upper section 248 of the vertically extending support 260, e.g., as shown in FIG. 18. In one embodiment the base portion 316b of the low profile support member 300 is connected at the socket 316a to the splined coupling adapter 316 by welding. If desired, the connection could be made in some other manner. Also, in one embodiment the base portion 316b of the low profile support member 300 which extends from the bend 312 into the socket 316a of the splined coupling adapter 316 is rather short; for example, the portion 316b may be just long enough to fit securely in the socket 316b and be attached to the splined coupling adapter to provide a secure connection therebetween. Thus, in one embodiment, the first horizontal extension 314 is directly connected to the splined coupling adaptor 316 substantially free of vertical rise therebetween, as shown, for example, in FIG. 19. In the embodiment shown in FIG. 19, the bend portion 312 is adjacent the splined coupling adaptor 316, as a result of which there is a minimal rise from the splined coupling adaptor 316 to the horizontal extension 314.

As shown in FIG. 19, the first horizontal extension 314 includes a plurality of bores 322 in the square segment 318. The square segment 318 is generally similar to the square segment 44 described with respect to FIG. 1 and the square segment 144 described with respect to FIG. 5. The bores 322 are adapted to receive a retaining member of a clamp (described below). In one embodiment, the first horizontal extension 314 includes the square segment 318 and a horizontal segment 324 which may be, for example, formed of round stock or other suitable stock, such as square, hexagonal, octagonal, or other cross-sectional shape. In one embodiment, the horizontal segment 324 is round stock, from which the square segment 318 is machined, prior to forming the bend 312.

As shown in FIG. 19, the splined coupling segment 316 includes a shallow recess 332, a coupling splined segment 334, a plurality of splines 335, a stop plug 336, and a deep recess 338. The splined coupling 316 in FIG. 19 differs from the splined coupling 230 in FIGS. 11 and 14 in that the deep recess 338 receives the key-like splined segment 228 of the lower section 220, whereas in the embodiment of the splined coupling segment 230 as described with respect to the embodiment shown in FIGS. 11 and 14, the shallow recess 232 receives the key-like splined segment 228. Thus, the embodiment shown in FIG. 19 simply represents a shift in the position of the splined segment 334 and the stop plug 336, and a reversal of the relative depths of the shallow recess 332 and the deep recess 338, relative to the corresponding parts in the embodiment shown in FIGS. 10–14.

The splined coupling 316 of the low profile support member 300 may be used with the lower portion 110 described with respect to FIGS. 4 and 8.

Figure 20:
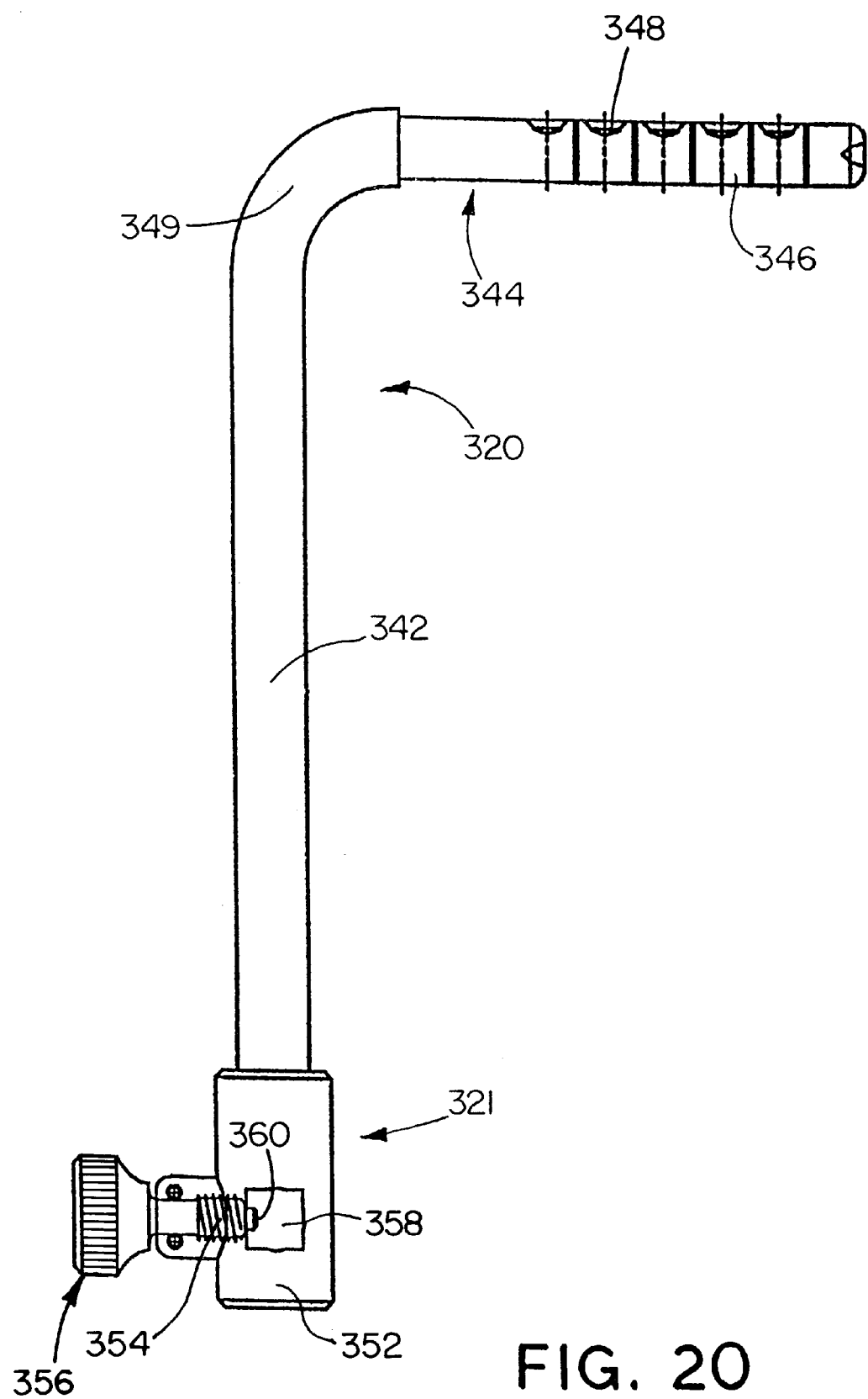
FIG. 20 is a side elevational view of an extender portion having both a vertical extension and a horizontal extension.

FIG. 20 is a side elevational view of an extender portion 320 having both a vertically extending section 342 and a second horizontal extension 344. The extender portion 320 is mountable on the first horizontal extension 320, by the clamp 321, described below.

In one embodiment, the vertically extending section 342 is formed of round stock. In one embodiment the round stock has a diameter of about ½ inch (about 1.25 cm), and in one embodiment has a diameter of ⅝ inch (about 1.6 cm). In other embodiments, the diameter of the round stock may be varied and selected as deemed necessary to obtain the needed retraction force while providing light weight parts. In one embodiment, the vertical extension 342 is formed of square stock having similar dimensions to the round stock. The vertically extending section 342 may be made of stock having other cross-sectional shapes, such as square, rectangular, hexagonal or octagonal.

The second horizontal extension 344 includes a square segment 346 which is generally similar to the square segments (44, 144, 318) described with respect to other embodiments of the present invention. The square segment 346 includes a plurality of bores 348, which are generally similar to the bores (48, 164, 322) described with respect to other embodiments of the present invention.

The second horizontal extension 344 is connected to the vertical extension 342 by a bend segment 349. The bend segment 349 is generally similar to the bend segment 312 described above with respect to the upper portion 310. In the embodiment shown in FIG. 20, the angle formed between the second horizontal extension 344 and the vertical extension 342 by the bend portion 348 is generally about 90°. In other embodiments, this angle may be varied as required for particular applications.

As shown in FIG. 20, in one embodiment, the extender portion 320 further includes the clamp 321. The clamp 321 is generally similar to the clamp 204 described above with respect to FIG. 9. In particular, the clamp 321 includes a clamp body 352, a threaded shaft 354, a handle 356, and a receptacle 358. The shaft 354 includes a lower end 360, opposite the handle, which is configured to securely fit into a positioning bore such as the bore 164 shown in and described with respect to FIGS. 7A and 7B. The clamp 321, as shown in FIG. 20, includes only the receptacle 358. However, the clamp 321, like the clamp 204, may include a second receptacle (not shown) so as to be adapted to retain the horizontal extension 320 in either receptacle. The shaft tip 360 on the threaded shaft 354 interacts with the bores 322 to retain the horizontal extension at a selected position in the clamp 321. Similarly, the shaft tip 360 may interact with the other bores described herein.

In one embodiment, the receptacle 352 is disposed such that the second horizontal extension 344 is mounted at a right angle to the first horizontal extension 314. In one embodiment, the receptacle 352 is disposed such that the second horizontal extension 344 is mounted parallel to the first horizontal extension 314.

In one embodiment, the splined coupling segment 316 enables the first horizontal extension 314 to be securely aligned at one of a plurality of selected angles with respect to the support platform 108. This feature has been described above with respect to FIGS. 10–14. The upper portion 310 of the low profile support member 300 is quite similar to the upper portion of the support members described with respect to other embodiments of the present invention. The upper portion is shown and described above with respect to FIGS. 15–17. Considering the upper portion 310 from the bend portion 312 to the first horizontal extension 314, i.e., the part above the spline portion 316, the upper portion 310 of the low profile support member 300 of the present embodiment is similar to the corresponding part of the vertically extending support device 36 described with respect to FIG. 1, except as noted above.

Figure 21:
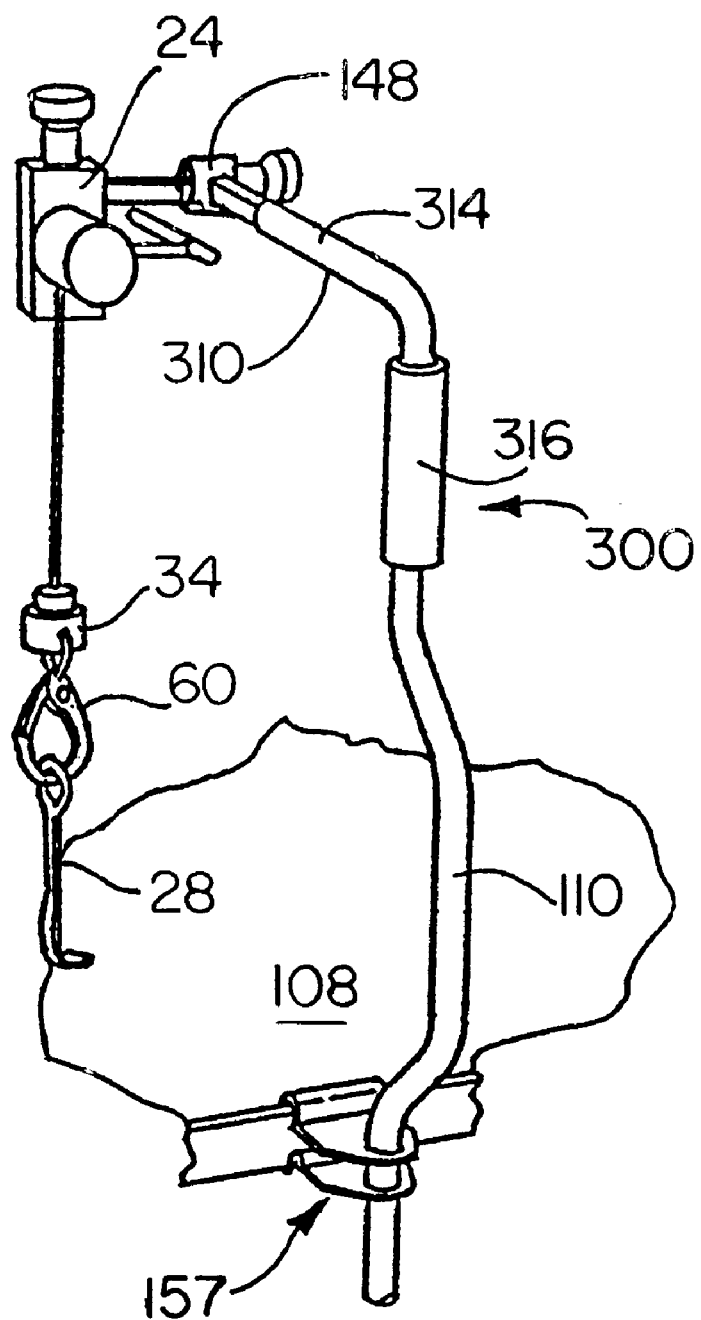
FIG. 21 is a perspective view of an embodiment of a low profile support member having a lower portion, an upper portion, an extender bar and a lifting device.

In one embodiment, shown in FIG. 21, the low profile support member 300 includes a lower portion 110, an upper portion 310, an extender bar 148, and a lifting device 24, but does not include an extender portion such as the extender portion 320. In this embodiment, in which the lifting device 24 is at a vertically lower position closer to the patient, a much more acute angle of retraction, with respect to the plane of the patient support 108 may be applied.

The present invention includes a method of providing surgical retraction to a patient positioned relative to a support platform 108, comprising the steps of mounting a lower portion 110 on the support platform 108 by an attachment clamp 157, mounting an upper portion 310 of the low-profile support member 300 with respect to the lower portion 110 by a lock-and-key-like splined connection and with respect to the support platform 108. The upper portion 310 comprises a first horizontal extension 314. The method includes mounting on the first horizontal extension 314 an extender portion 320 having both a vertical extension 342 and a second horizontal extension 344. The method includes positioning a lifting device 24 above a patient on the support platform 108 by mounting the lifting device 24 with respect to the second horizontal extension 344. When the lifting device 24 is mounted and attached to the patient, for example, by means of the retractor apparatus 26, 28 shown in FIG. 16, retraction may be applied to the patient. In one embodiment of the method, the step of mounting the upper portion 310 further comprises selecting a desired angle of orientation between the first horizontal extension 314 and the support platform.

Thus, in this method, the surgical team may first mount the lower portion 110 on the support platform 108, by any of the standard means, such as the clamp 157 described hereinabove. Next, the upper portion 310 may be mounted upon the lower portion 110. Due to the splined coupling 316, it is possible to select the angle between the first horizontal extension 314 of the upper portion 310 with respect to the patient and the longitudinal direction of the support platform 108 from a plurality of such possible angles. The angle between the first horizontal extension 314 and the longitudinal direction of the support platform 108, and thus the position of the lifting device 24 relative to the patient, may be selected at the time of initial mounting and may be adjusted at any time. After the upper portion 310 has been securely mounted, the extender portion 320 having both a vertical extension 342 and a second horizontal extension 344 may be mounted on and clamped by the clamp 321 to the first horizontal extension 314. The lifting device 24 may be mounted with respect to the second horizontal extension 344 above the patient at any time before or after mounting the extender portion 320 on the first horizontal extension 314. As mentioned above, the lifting device 24 may be positioned above the patient at the time of initial mounting, or at any later time, and may be adjusted or repositioned at any time, by mounting the lifting device 24 with respect to the second horizontal extension 344, which thereby is placed into an angular relation between a first one of the parts, e.g., the upper portion 310, and a second one of the parts, e.g., the lower portion 110, at the lock-and-key-like splined connection 316. Thereafter, the lifting device 24 may be operably attached to the patient and retraction applied to the patient as needed by the surgical team.

The present invention includes a further embodiment of a method of providing surgical retraction to a patient positioned relative to a support platform 108, comprising the steps of positioning a lifting device 24 above the patient, in which the positioning includes mounting the lifting device 24 on a multiple part generally vertically extending low profile support member 300 which has a lock-and-key-like splined connection 316 between at least two of the multiple parts, e.g., the upper portion 310 and the lower portion 110. The support member 300 includes a first horizontal extension 314. The method includes the step of mounting on the first horizontal extension 314 an extender portion 320 having both a vertical extension 342 and a second horizontal extension 344. When the lifting device 24 is mounted, the position of the lifting device 24 relative to the patient may be adjusted by selecting an angular relation between a first one of the parts, e.g., the upper portion 310, and a second one of the parts, e.g., the lower portion 110, at the lock-and-key-like splined connection 316. When the lifting device 24 has been mounted and adjusted, retraction may be applied to the patient. In one embodiment, the step of mounting includes placing the lifting device 24 on the second horizontal extension 344.

Thus, in this embodiment of the method, the surgical team positions the lifting device 24 above the patient by mounting the lifting device 24 on the multiple part low profile support member 300, which includes a lock-and-key-like splined connection 316 between at least two of the parts, e.g., the upper portion 310 and the lower portion 110. The low profile support member 300 extends generally vertically above the patient. As described above, the surgical team may mount the lower member 110 and the upper member 310 of the low profile support member 316 with respect to the support apparatus 108, i.e., the surgical table. The surgical team may mount an extender portion 320 on the first horizontal extension 314 of the upper portion 310. The surgical team may mount the lifting device 24 on the second horizontal extension 344, and attach the lifting device 24 thereto by the clamp 321. At this point, or at another point in the procedure, the surgical team may adjust the position of the lifting device 24 relative to the patient by selecting an angular relation between a first one of the parts, e.g., the upper portion 310, and a second one of the parts, e.g., the lower portion 110, of the low profile support member 300 by adjusting the angle formed by the lock-and-key-like splined connection 316. Thereafter, retraction may be applied to the patient.

Using a retractor with a low profile support member 300, if desired, the retraction effort can be applied at a more acute angle than with the higher profile retractor. Also, there is greater available area in the surgical field for the surgical team to move about and to operate on the patient during the surgical procedure, this being especially advantageous in the case of surgeries for relatively small size patients, such as children.

The low profile support member 300, as described above, allows use of a surgical retraction device and is particularly adaptable to specialized uses such as pediatric surgery, in which it may be necessary to introduce novel techniques due to relatively small size of the patient. The low profile support member 300, used as described herein, allows a surgeon to adapt surgical procedures and apparatus originally designed for adult patients for use with pediatric patients. For example, the low profile support member 300 allows the surgeon to adjust the angle of and direction from which retraction is applied. Thus, by changing the support member from a standard, relatively high support such as the support member 260, the surgeon can adapt surgical procedures and apparatus to additional uses, such as pediatric surgery, without being forced to make significant changes in the retraction apparatus.

As additional significant benefit of the low profile support member 300 and the methods of using it is the additional space in the surgical field which is made available. Because a significant portion of the vertical aspect of the low profile support member is located toward the center, away from the sides, of the surgical support platform, the surgical team is allowed more "elbow room" in the area in which they must stand, the sides of the surgical support platform.

Variations on the foregoing methods may be made, including changes in the order in which the low profile support member 300 and the lifting device 24 are assembled, as needed in a particular situation, without departing from the scope of the present method.

Although the invention has been shown and described with respect to certain embodiments, it is obvious that equivalents and modifications will occur to others skilled in the art upon the reading and understanding of the specification. The present invention includes all such equivalents and modifications, and is limited only by the scope of the following claims.

What is claimed is:

1. A low profile support member for a surgical retraction apparatus, comprising
   a lower portion mountable on a support platform;
   an upper portion of the low profile support member having a first horizontal extension;
   a splined coupling adaptor for connecting the lower portion and the upper portions, wherein the adaptor comprises a splined segment having a key-like splined portion and a lock-like splined portion; and
   an extender portion having both a vertical extension and a second horizontal extension, the extender portion mountable on the first horizontal extension.

2. The support member of claim 1, wherein the extender portion further comprises a clamp and a receptacle for receiving the first horizontal extension.

3. The support member of claim 2, wherein the receptacle is disposed such that the second horizontal extension is mounted at a right angle to the first horizontal extension.

4. The support member of claim 1, wherein the first horizontal extension is directly connected to the splined coupling adaptor with relatively minimal vertical rise therebetween.

5. The support member of claim 1, wherein the first horizontal extension is directly connected to the splined coupling adaptor substantially free of vertical rise therebetween.

6. The support member of claim 1, wherein a base portion of the low profile support member is just long enough to fit securely in and be attached to the splined coupling adapter.

7. The support member of claim 1 wherein the splined coupling adaptor enables the first horizontal extension to be securely aligned at one of a plurality of selected angles with respect to the anchoring receptacle.

8. A method of providing surgical retraction to a patient positioned relative to a support platform, comprising the steps of:
   mounting upper and lower portions of a low-profile support member with respect to each other by a lock-and-key-like splined connection and with respect to the platform, the upper portion comprising a first horizontal extension;
   mounting on the first horizontal extension an extender portion having both a vertical extension and a second horizontal extension;
   positioning a lifting device above the patient by mounting the lifting device with respect to the second horizontal extension; and
   applying retraction to the patient.

9. The method of claim 8, wherein the step of upper and lower portions mounting further comprises selecting a desired angle of orientation between the first horizontal extension and the support platform.

10. The method of claim 8, further comprising selecting a desired angle from which retraction is applied to the patient.

11. The method of claim 8, wherein the step of mounting on the first horizontal extension an extender portion places the vertical extension in a position substantially aligned with a patient midline plane.

12. A method of providing surgical retraction to a patient positioned relative to a support platform, comprising the steps of:
    positioning a lifting device above the patient, said positioning comprising mounting the lifting device on a multiple part generally vertically extending low profile support member which has a lock-and-key-like splined connection between at least two of the multiple parts, the support member comprising a first horizontal extension, and mounting on the first horizontal extension an extender portion having both a vertical extension and a second horizontal extension;
    adjusting the position of the lifting device relative to the patient by selecting an angular relation between a first one of the parts and a second one of the parts at the lock-and-key-like splined connection; and
    applying retraction to the patient.

13. A method as in claim 12, wherein the step of mounting the lifting device comprises placing the lifting device on the second horizontal extension.

14. The method of claim 12, wherein the step of mounting the lifting device further comprises selecting a desired angle of orientation between the first horizontal extension and the support platform.

15. The method of claim 12, further comprising selecting a desired angle at which retraction is applied to the patient.

16. The method of claim 12, wherein the step of mounting on the first horizontal extension an extender portion places the vertical extension in a position substantially aligned with a patient midline plane.

* * * * *